US009402533B2

(12) United States Patent
Kirma et al.

(10) Patent No.: US 9,402,533 B2
(45) Date of Patent: Aug. 2, 2016

(54) ENDOSCOPE CIRCUIT BOARD ASSEMBLY

(75) Inventors: Yaniv Kirma, Tzrufa (IL); Moshe Levi, Gane Tikva (IL); Leonid Krivopisk, Nesher (IL); Avi Levy, Herzliya (IL)

(73) Assignee: ENDOCHOICE INNOVATION CENTER LTD., Caesarea (IL)

( * ) Notice: Subject to any disclaimer, the term of this patent is extended or adjusted under 35 U.S.C. 154(b) by 495 days.

(21) Appl. No.: 13/413,059

(22) Filed: Mar. 6, 2012

(65) Prior Publication Data
US 2012/0229615 A1    Sep. 13, 2012

Related U.S. Application Data

(60) Provisional application No. 61/449,741, filed on Mar. 7, 2011.

(51) Int. Cl.
*A61B 1/04* (2006.01)
*A61B 1/06* (2006.01)
*A61B 1/00* (2006.01)
*A61B 1/05* (2006.01)

(52) U.S. Cl.
CPC .............. *A61B 1/00181* (2013.01); *A61B 1/051* (2013.01)

(58) Field of Classification Search
CPC .... A61B 1/00181; A61B 1/051; A61B 1/015; A61B 1/05; A61B 1/041; A61B 1/0638; A61B 1/0676; A61B 1/0684; A61B 1/126
USPC ......... 600/129, 153, 155, 156, 158, 160, 166, 600/178; 348/76
See application file for complete search history.

(56) References Cited

U.S. PATENT DOCUMENTS

| | | |
|---|---|---|
| 4,253,448 A | 3/1981 | Terada |
| 4,261,345 A | 4/1981 | Yamaguchi |
| 4,402,313 A | 9/1983 | Yabe |
| 4,414,608 A | 11/1983 | Furihata |
| 4,439,030 A | 3/1984 | Ueda |
| 4,469,090 A | 9/1984 | Konomura |
| 4,494,549 A | 1/1985 | Namba |
| 4,522,196 A | 6/1985 | Cunningham |
| 4,565,423 A | 1/1986 | Ueda |
| 4,576,144 A | 3/1986 | Ishii |

(Continued)

FOREIGN PATENT DOCUMENTS

| | | |
|---|---|---|
| CN | 1988841 | 6/2007 |
| CN | 101061940 A | 10/2007 |

(Continued)

OTHER PUBLICATIONS

Office Action dated May 30, 2014 for U.S. Appl. No. 13/119,032.

(Continued)

*Primary Examiner* — Thomas J Sweet
*Assistant Examiner* — Arnaldo Torres Diaz
(74) *Attorney, Agent, or Firm* — Novel IP

(57) ABSTRACT

There is provided herein a circuit board assembly for a tip section of a multi-camera endoscope comprising a camera circuit board configured to carry at least one front-pointing camera and at least one side-pointing camera, a flexible illuminator circuit board comprising at least one foldable panel and configured to carry at least one front illuminator for essentially illuminating the field of view (FOV) of the front-pointing camera and at least one side illuminator for essentially illuminating the FOV of the side-pointing camera.

21 Claims, 18 Drawing Sheets

(56) References Cited

U.S. PATENT DOCUMENTS

| | | | |
|---|---|---|---|
| 4,588,294 | A | 5/1986 | Siegmund |
| 4,590,923 | A | 5/1986 | Watanabe |
| 4,641,635 | A | 2/1987 | Yabe |
| 4,699,463 | A | 10/1987 | D'Amelio et al. |
| 4,708,126 | A | 11/1987 | Toda |
| 4,736,732 | A | 4/1988 | Shimonaka |
| 4,753,222 | A | 6/1988 | Morishita |
| 4,764,001 | A | 8/1988 | Yokota |
| 4,794,913 | A | 1/1989 | Shimonaka |
| 4,801,792 | A | 1/1989 | Yamasita |
| 4,841,952 | A | 6/1989 | Sato |
| 4,846,154 | A | 7/1989 | MacAnally |
| 4,868,644 | A | 9/1989 | Yabe |
| 4,877,314 | A | 10/1989 | Kanamori |
| 4,878,485 | A | 11/1989 | Adair |
| 4,888,639 | A | 12/1989 | Yabe |
| 4,902,115 | A | 2/1990 | Takahashi |
| 4,905,670 | A | 3/1990 | Adair |
| 4,914,521 | A | 4/1990 | Adair |
| 4,974,075 | A | 11/1990 | Nakajima |
| 4,976,522 | A | 12/1990 | Igarashi |
| 4,982,724 | A | 1/1991 | Saito |
| 4,984,878 | A | 1/1991 | Miyano |
| 4,998,182 | A | 3/1991 | Krauter |
| 5,166,787 | A | 11/1992 | Irion |
| 5,193,525 | A | 3/1993 | Silverstein |
| 5,239,983 | A | 8/1993 | Katsurada |
| 5,296,971 | A | 3/1994 | Mori |
| 5,299,561 | A | 4/1994 | Yoshimoto |
| 5,305,121 | A | 4/1994 | Moll |
| 5,309,227 | A | 5/1994 | Inoue |
| 5,313,934 | A | 5/1994 | Wiita |
| 5,339,800 | A | 8/1994 | Wiita |
| 5,359,456 | A | 10/1994 | Kikuchi |
| 5,380,049 | A | 1/1995 | Smowton |
| 5,398,056 | A | 3/1995 | Yabe |
| 5,408,623 | A | 4/1995 | Dolidon |
| 5,412,478 | A | 5/1995 | Ishihara |
| 5,420,644 | A | 5/1995 | Watanabe |
| 5,432,543 | A | 7/1995 | Hasegawa |
| 5,436,767 | A | 7/1995 | Suzuki |
| 5,447,148 | A | 9/1995 | Oneda |
| 5,452,391 | A | 9/1995 | Chou |
| 5,460,167 | A | 10/1995 | Yabe |
| 5,483,951 | A | 1/1996 | Frassica |
| 5,485,316 | A | 1/1996 | Mori |
| 5,489,256 | A | 2/1996 | Adair |
| 5,507,717 | A | 4/1996 | Kura |
| 5,512,940 | A | 4/1996 | Takasugi |
| 5,515,449 | A | 5/1996 | Tsuruoka |
| 5,518,501 | A | 5/1996 | Oneda |
| 5,518,502 | A | 5/1996 | Kaplan |
| 5,547,455 | A | 8/1996 | McKenna |
| 5,547,457 | A | 8/1996 | Tsuyuki |
| 5,550,582 | A | 8/1996 | Takasugi |
| 5,585,840 | A | 12/1996 | Watanabe |
| 5,587,839 | A | 12/1996 | Miyano |
| 5,589,874 | A | 12/1996 | Buchin |
| 5,592,216 | A | 1/1997 | Uehara |
| 5,605,530 | A | 2/1997 | Fischell |
| 5,609,560 | A | 3/1997 | Ichikawa |
| 5,617,136 | A | 4/1997 | Iso |
| 5,630,782 | A | 5/1997 | Adair |
| 5,653,677 | A | 8/1997 | Okada |
| 5,656,011 | A | 8/1997 | Uihlein |
| 5,675,378 | A | 10/1997 | Takasugi |
| 5,679,110 | A | 10/1997 | Hamazaki |
| 5,685,823 | A | 11/1997 | Ito |
| 5,701,155 | A | 12/1997 | Wood |
| 5,702,345 | A | 12/1997 | Wood |
| 5,702,347 | A | 12/1997 | Yabe |
| 5,716,323 | A | 2/1998 | Lee |
| 5,725,474 | A | 3/1998 | Yasui |
| 5,725,476 | A | 3/1998 | Yasui |
| 5,725,477 | A | 3/1998 | Yasui |
| 5,728,045 | A | 3/1998 | Komi |
| 5,751,340 | A | 5/1998 | Strobl |
| 5,764,809 | A | 6/1998 | Nomami |
| 5,777,797 | A | 7/1998 | Miyano |
| 5,782,751 | A | 7/1998 | Matsuno |
| 5,793,539 | A | 8/1998 | Konno |
| 5,800,341 | A | 9/1998 | McKenna |
| 5,812,187 | A | 9/1998 | Watanabe |
| 5,830,124 | A | 11/1998 | Suzuki |
| 5,852,511 | A | 12/1998 | Tateyama |
| 5,870,234 | A | 2/1999 | Ebbesmeier |
| 5,871,439 | A | 2/1999 | Takahashi |
| 5,876,326 | A | 3/1999 | Takamura |
| 5,879,284 | A | 3/1999 | Tsujita |
| 5,894,322 | A | 4/1999 | Hamano |
| 5,912,764 | A | 6/1999 | Togino |
| 5,913,817 | A | 6/1999 | Lee |
| 5,914,810 | A | 6/1999 | Watts |
| 5,916,148 | A | 6/1999 | Tsuyuki |
| 5,929,901 | A | 7/1999 | Adair |
| 5,930,424 | A | 7/1999 | Heimberger |
| 5,933,275 | A | 8/1999 | Igarashi |
| 5,933,282 | A | 8/1999 | Tomioka |
| 5,936,773 | A | 8/1999 | Togino |
| 5,940,126 | A | 8/1999 | Kimura |
| 5,961,445 | A | 10/1999 | Chikama |
| 5,969,888 | A | 10/1999 | Sukekawa |
| 5,986,693 | A | 11/1999 | Adair |
| 5,989,185 | A | 11/1999 | Miyazaki |
| 5,993,037 | A | 11/1999 | Tomioka |
| 5,995,136 | A | 11/1999 | Hattori |
| 6,009,189 | A | 12/1999 | Schaack |
| 6,025,873 | A | 2/2000 | Nishioka |
| 6,043,839 | A | 3/2000 | Adair |
| 6,069,698 | A | 5/2000 | Ozawa |
| 6,080,104 | A | 6/2000 | Ozawa |
| 6,104,540 | A | 8/2000 | Hayakawa |
| 6,110,127 | A | 8/2000 | Suzuki |
| 6,124,989 | A | 9/2000 | Oode |
| 6,139,175 | A | 10/2000 | Tomioka |
| 6,139,490 | A | 10/2000 | Breidenthal |
| 6,147,808 | A | 11/2000 | Togino |
| 6,163,401 | A | 12/2000 | Igarashi |
| 6,166,858 | A | 12/2000 | Togino |
| 6,181,481 | B1 | 1/2001 | Yamamoto |
| 6,184,923 | B1 | 2/2001 | Miyazaki |
| 6,185,046 | B1 | 2/2001 | Togino |
| 6,201,646 | B1 | 3/2001 | Togino |
| 6,201,648 | B1 | 3/2001 | Togino |
| 6,210,322 | B1 | 4/2001 | Byrne |
| 6,211,904 | B1 | 4/2001 | Adair |
| 6,215,517 | B1 | 4/2001 | Takahashi |
| 6,217,500 | B1 | 4/2001 | Helseth |
| 6,245,086 | B1 | 6/2001 | Storz |
| 6,249,391 | B1 | 6/2001 | Hayakawa |
| 6,260,994 | B1 | 7/2001 | Matsumoto |
| 6,261,226 | B1 | 7/2001 | McKenna |
| 6,275,255 | B1 | 8/2001 | Adair |
| 6,295,368 | B1 | 9/2001 | Hasegawa |
| 6,306,082 | B1 | 10/2001 | Takahashi |
| 6,310,642 | B1 | 10/2001 | Adair |
| 6,310,736 | B1 | 10/2001 | Togino |
| 6,315,712 | B1 | 11/2001 | Rovegno |
| 6,322,496 | B1 | 11/2001 | Iida |
| 6,327,094 | B1 | 12/2001 | Aoki |
| 6,327,101 | B1 | 12/2001 | Miyano |
| 6,334,845 | B1 | 1/2002 | Higuchi |
| 6,353,504 | B1 | 3/2002 | Yamamoto |
| 6,387,045 | B1 | 5/2002 | Takahashi |
| 6,398,723 | B1 | 6/2002 | Kehr |
| 6,400,514 | B2 | 6/2002 | Minami |
| 6,422,995 | B2 | 7/2002 | Akiba |
| 6,425,857 | B1 | 7/2002 | Rudischhauser |
| 6,450,950 | B2 | 9/2002 | Irion |
| 6,461,304 | B1 | 10/2002 | Tanaka |
| 6,464,631 | B1 | 10/2002 | Girke |
| 6,464,633 | B1 | 10/2002 | Hosoda |
| 6,468,201 | B1 | 10/2002 | Burdick |
| 6,468,202 | B1 | 10/2002 | Irion |

(56) References Cited

U.S. PATENT DOCUMENTS

| | | |
|---|---|---|
| 6,471,636 B1 | 10/2002 | Sano |
| 6,471,637 B1 | 10/2002 | Green |
| 6,473,116 B1 | 10/2002 | Takahashi |
| 6,476,851 B1 | 11/2002 | Nakamura |
| 6,500,115 B2 | 12/2002 | Krattiger |
| 6,514,210 B2 | 2/2003 | Ohara |
| 6,520,908 B1 | 2/2003 | Ikeda |
| 6,527,704 B1 | 3/2003 | Chang |
| 6,530,881 B1 | 3/2003 | Ailinger |
| 6,533,722 B2 | 3/2003 | Nakashima |
| 6,545,703 B1 | 4/2003 | Takahashi |
| 6,551,239 B2 | 4/2003 | Renner |
| 6,554,767 B2 | 4/2003 | Tanaka |
| 6,567,114 B2 | 5/2003 | Takahashi |
| 6,569,084 B1 | 5/2003 | Mizuno |
| 6,582,361 B2 | 6/2003 | Hirano |
| 6,589,168 B2 | 7/2003 | Thompson |
| 6,606,113 B2 | 8/2003 | Nakamura |
| 6,618,205 B2 | 9/2003 | Murayama |
| D481,125 S | 10/2003 | Hayamizu |
| 6,638,212 B1 | 10/2003 | Oshima |
| 6,638,214 B2 | 10/2003 | Akiba |
| 6,641,531 B2 | 11/2003 | Kehr |
| 6,656,111 B2 | 12/2003 | Fujii |
| 6,671,099 B2 | 12/2003 | Nagata |
| 6,677,983 B1 | 1/2004 | Takahashi |
| 6,677,984 B2 | 1/2004 | Kobayashi |
| 6,677,992 B1 | 1/2004 | Matsumoto |
| 6,692,430 B2 | 2/2004 | Adler |
| 6,692,431 B2 | 2/2004 | Kazakevich |
| 6,699,181 B2 | 3/2004 | Wako |
| 6,699,185 B2 | 3/2004 | Gminder |
| 6,704,052 B1 | 3/2004 | Togino |
| 6,712,760 B2 | 3/2004 | Sano |
| D490,898 S | 6/2004 | Hayamizu |
| 6,764,439 B2 | 7/2004 | Schaaf |
| 6,778,208 B2 | 8/2004 | Takeshige |
| 6,788,343 B1 | 9/2004 | Togino |
| 6,793,621 B2 | 9/2004 | Butler |
| 6,801,325 B2 | 10/2004 | Farr |
| 6,809,499 B2 | 10/2004 | Solingen |
| 6,809,866 B2 | 10/2004 | Xie |
| 6,829,003 B2 | 12/2004 | Takami |
| 6,832,984 B2 | 12/2004 | Stelzer |
| 6,844,985 B2 | 1/2005 | Murayama |
| 6,846,311 B2 | 1/2005 | Gatto |
| 6,849,043 B2 | 2/2005 | Kondo |
| 6,860,516 B2 | 3/2005 | Ouchi |
| 6,876,380 B2 | 4/2005 | Abe |
| 6,887,194 B2 | 5/2005 | Hart |
| 6,888,119 B2 | 5/2005 | Iizuka |
| 6,898,086 B2 | 5/2005 | Takami |
| 6,899,673 B2 | 5/2005 | Ogura |
| 6,900,829 B1 | 5/2005 | Ozawa |
| 6,900,950 B2 | 5/2005 | Nagata |
| 6,902,529 B2 | 6/2005 | Onishi |
| 6,903,761 B1 | 6/2005 | Abe |
| 6,918,693 B2 | 7/2005 | Ota |
| 6,921,362 B2 | 7/2005 | Ouchi |
| 6,930,705 B2 | 8/2005 | Tanaka |
| 6,933,962 B2 | 8/2005 | Yamamoto |
| 6,937,267 B1 | 8/2005 | Takahashi |
| 6,937,269 B2 | 8/2005 | Sugimoto |
| 6,943,821 B2 | 9/2005 | Abe |
| 6,943,822 B2 | 9/2005 | Iida |
| 6,944,031 B2 | 9/2005 | Takami |
| 6,945,929 B2 | 9/2005 | Ando |
| 6,947,070 B2 | 9/2005 | Takami |
| 6,950,691 B2 | 9/2005 | Uchikubo |
| 6,956,703 B2 | 10/2005 | Saito |
| 6,967,673 B2 | 11/2005 | Ozawa |
| 6,977,670 B2 | 12/2005 | Takahashi |
| 6,980,227 B2 | 12/2005 | Iida |
| 6,982,740 B2 | 1/2006 | Adair |
| 6,985,170 B1 | 1/2006 | Tsuyuki |
| 6,992,694 B2 | 1/2006 | Abe |
| 6,995,786 B2 | 2/2006 | Abe |
| 6,997,871 B2 | 2/2006 | Sonnenschein |
| 7,027,231 B2 | 4/2006 | Miyano |
| 7,030,904 B2 | 4/2006 | Adair |
| 7,037,258 B2 | 5/2006 | Chatenever |
| 7,042,488 B2 | 5/2006 | Higuchi |
| 7,043,153 B2 | 5/2006 | Takeyama |
| 7,046,270 B2 | 5/2006 | Murata |
| 7,050,086 B2 | 5/2006 | Ozawa |
| 7,074,181 B2 | 7/2006 | Futatsugi |
| 7,074,182 B2 | 7/2006 | Rovegno |
| 7,085,064 B2 | 8/2006 | Uzawa |
| 7,097,615 B2 | 8/2006 | Banik |
| 7,104,951 B2 | 9/2006 | Hasegawa |
| 7,108,656 B2 | 9/2006 | Fujikawa |
| 7,108,657 B2 | 9/2006 | Irion |
| 7,119,830 B2 | 10/2006 | Saito |
| 7,123,288 B2 | 10/2006 | Abe |
| 7,128,709 B2 | 10/2006 | Saruya |
| 7,129,472 B1 | 10/2006 | Okawa |
| 7,133,063 B2 | 11/2006 | Abe |
| D534,656 S | 1/2007 | Pilvisto |
| 7,156,863 B2 | 1/2007 | Sonnenschein |
| 7,158,314 B2 | 1/2007 | Fujii |
| 7,179,221 B2 | 2/2007 | Tsujita |
| 7,180,686 B2 | 2/2007 | Kato |
| 7,218,454 B2 | 5/2007 | Miyano |
| 7,223,231 B2 | 5/2007 | Akiba |
| 7,231,135 B2 | 6/2007 | Esenyan |
| 7,232,409 B2 | 6/2007 | Hale |
| 7,233,820 B2 | 6/2007 | Gilboa |
| 7,242,833 B2 | 7/2007 | Yang |
| 7,248,281 B2 | 7/2007 | Abe |
| 7,248,296 B2 | 7/2007 | Iketani |
| 7,252,633 B2 | 8/2007 | Obata |
| 7,255,676 B2 | 8/2007 | Higuchi |
| 7,262,797 B2 | 8/2007 | Weldum |
| 7,267,647 B2 | 9/2007 | Okada |
| 7,273,452 B2 | 9/2007 | Barbato |
| 7,277,120 B2 | 10/2007 | Gere |
| 7,280,140 B2 | 10/2007 | Henderson |
| 7,280,283 B1 | 10/2007 | Kasai |
| 7,282,025 B2 | 10/2007 | Abe |
| 7,306,588 B2 | 12/2007 | Loeb |
| 7,330,749 B1 | 2/2008 | Bhunachet |
| D564,659 S | 3/2008 | Hayashi |
| D564,660 S | 3/2008 | Hayashi |
| 7,351,202 B2 | 4/2008 | Long |
| 7,355,625 B1 | 4/2008 | Mochida |
| 7,358,987 B2 | 4/2008 | Takeshige |
| 7,365,768 B1 | 4/2008 | Ono |
| 7,371,211 B2 | 5/2008 | Akiba |
| 7,379,252 B2 | 5/2008 | Murayama |
| 7,384,308 B2 | 6/2008 | Boehnlein |
| 7,399,304 B2 | 7/2008 | Gambale |
| 7,400,341 B2 | 7/2008 | Abe |
| 7,401,984 B2 | 7/2008 | Pattie |
| 7,409,130 B2 | 8/2008 | Hatori |
| 7,420,586 B2 | 9/2008 | Higuchi |
| 7,427,263 B2 | 9/2008 | Hoeg |
| 7,431,619 B2 | 10/2008 | Boehnlein |
| 7,435,217 B2 | 10/2008 | Wiklof |
| 7,435,218 B2 | 10/2008 | Krattiger |
| 7,440,005 B2 | 10/2008 | Enomoto |
| 7,443,488 B2 | 10/2008 | Ogawa |
| 7,450,151 B2 | 11/2008 | Kaneko |
| 7,466,490 B2 | 12/2008 | Igarashi |
| 7,471,310 B2 | 12/2008 | Amling |
| 7,484,709 B2 | 2/2009 | Efinger |
| 7,486,449 B2 | 2/2009 | Miyano |
| 7,492,388 B2 | 2/2009 | Odlivak |
| 7,514,667 B2 | 4/2009 | Matsumoto |
| 7,518,632 B2 | 4/2009 | Konomura |
| 7,530,948 B2 | 5/2009 | Seibel |
| 7,542,069 B2 | 6/2009 | Tashiro |
| 7,553,276 B2 | 6/2009 | Iddan |
| 7,559,889 B2 | 7/2009 | Takahashi |
| 7,559,892 B2 | 7/2009 | Adler |

(56) References Cited

U.S. PATENT DOCUMENTS

| | | | |
|---|---|---|---|
| 7,561,351 B2 | 7/2009 | Konno |
| 7,569,012 B2 | 8/2009 | Tanaka |
| 7,573,499 B2 | 8/2009 | Doguchi |
| 7,576,310 B2 | 8/2009 | Konno |
| 7,581,988 B2 | 9/2009 | Boehnlein |
| 7,582,055 B2 | 9/2009 | Komiya |
| 7,582,056 B2 | 9/2009 | Noguchi |
| 7,584,534 B2 | 9/2009 | Pease |
| 7,585,274 B2 | 9/2009 | Homma |
| 7,588,535 B2 | 9/2009 | Adler |
| 7,593,051 B2 | 9/2009 | Suda |
| 7,621,868 B2 | 11/2009 | Breidenthal |
| 7,621,869 B2 | 11/2009 | Ratnakar |
| 7,623,150 B2 | 11/2009 | Kobayashi |
| 7,627,189 B2 | 12/2009 | Donomae |
| 7,630,148 B1 | 12/2009 | Yang |
| 7,671,888 B2 | 3/2010 | Nogami |
| 7,683,927 B2 | 3/2010 | Higuchi |
| 7,695,429 B2 | 4/2010 | Hino |
| 7,699,772 B2 | 4/2010 | Pauker |
| 7,701,650 B2 | 4/2010 | Lin |
| 7,725,013 B2 | 5/2010 | Sugimoto |
| 7,728,867 B2 | 6/2010 | Fukuyama |
| 7,734,160 B2 | 6/2010 | Sudo |
| 7,746,566 B2 | 6/2010 | Mizusawa |
| 7,746,572 B2 | 6/2010 | Asami |
| 7,749,156 B2 | 7/2010 | Ouchi |
| 7,749,159 B2 | 7/2010 | Crowley |
| 7,758,495 B2 | 7/2010 | Pease |
| 7,758,499 B2 | 7/2010 | Adler |
| 7,772,786 B2 | 8/2010 | Hosoda |
| 7,773,110 B2 | 8/2010 | Abe |
| 7,773,122 B2 | 8/2010 | Irion |
| 7,773,318 B2 | 8/2010 | Takato |
| 7,775,971 B2 | 8/2010 | Fujimori |
| 7,775,973 B2 | 8/2010 | Okada |
| 7,789,822 B2 | 9/2010 | Suzuki |
| 7,800,656 B2 | 9/2010 | Takeuchi |
| RE41,807 E | 10/2010 | Yokoi |
| 7,821,529 B2 | 10/2010 | Mochida |
| 7,837,614 B2 | 11/2010 | Segawa |
| 7,841,880 B2 | 11/2010 | Ikeda |
| 7,846,090 B2 | 12/2010 | Pilvisto |
| 7,852,513 B2 | 12/2010 | Donomae |
| 7,893,956 B2 | 2/2011 | Ayrenschmalz |
| 7,896,802 B2 | 3/2011 | Otawara |
| 7,901,352 B2 | 3/2011 | Minami |
| 7,907,168 B2 | 3/2011 | Eino |
| 7,907,170 B2 | 3/2011 | Watanabe |
| 7,907,352 B2 | 3/2011 | Miyano |
| 7,914,443 B2 | 3/2011 | Uchimura |
| 7,918,788 B2 | 4/2011 | Lin |
| 7,938,773 B2 | 5/2011 | Kawai |
| 7,940,296 B2 | 5/2011 | Ogino |
| 7,942,814 B2 | 5/2011 | Remijan |
| 7,951,068 B2 | 5/2011 | Kura |
| 7,967,745 B2 * | 6/2011 | Gilad ............................ 600/160 |
| 7,976,462 B2 | 7/2011 | Wright |
| 7,995,093 B2 | 8/2011 | Takeuchi |
| 7,998,064 B2 | 8/2011 | Otawara |
| 8,002,696 B2 | 8/2011 | Suzuki |
| 8,027,101 B2 | 9/2011 | Suda |
| 8,033,992 B2 | 10/2011 | Hino |
| 8,035,684 B2 | 10/2011 | Wakito |
| 8,038,600 B2 | 10/2011 | Uchiyama |
| 8,043,207 B2 | 10/2011 | Adams |
| 8,060,172 B2 | 11/2011 | Ishihara |
| 8,063,962 B2 | 11/2011 | Hagihara |
| 8,066,631 B2 | 11/2011 | Wimmer |
| 8,072,483 B2 | 12/2011 | Tomioka |
| 8,072,537 B2 | 12/2011 | Schwarz |
| 8,072,693 B2 | 12/2011 | Togino |
| 8,075,477 B2 | 12/2011 | Nakamura |
| 8,075,478 B2 | 12/2011 | Campos |
| 8,098,441 B2 | 1/2012 | Sasamoto |
| 8,100,920 B2 | 1/2012 | Gambale |
| 8,102,415 B2 | 1/2012 | Iriyama |
| 8,105,233 B2 | 1/2012 | AbouElKheir |
| 8,113,846 B2 | 2/2012 | Wallaker |
| 8,125,514 B2 | 2/2012 | Sekiguchi |
| 8,125,515 B2 | 2/2012 | Hibi |
| 8,130,454 B2 | 3/2012 | Noguchi |
| 8,135,192 B2 | 3/2012 | Matsuzaki |
| 8,135,454 B2 | 3/2012 | Daniels |
| 8,139,296 B2 | 3/2012 | Ito |
| 8,144,191 B2 | 3/2012 | Kawanishi |
| 8,149,274 B2 | 4/2012 | Yamazaki |
| 8,152,718 B2 | 4/2012 | Cheng |
| 8,152,821 B2 | 4/2012 | Gambale |
| 8,157,798 B2 | 4/2012 | Takahashi |
| 8,164,836 B2 | 4/2012 | Uzawa |
| 8,167,791 B2 | 5/2012 | Tanaka |
| 8,167,795 B2 | 5/2012 | Hoeg |
| 8,167,796 B2 | 5/2012 | Negishi |
| 8,182,419 B2 | 5/2012 | Kohno |
| 8,187,171 B2 | 5/2012 | Irion |
| 8,187,174 B2 | 5/2012 | Wang |
| 8,189,041 B2 | 5/2012 | Konishi |
| 8,189,062 B2 | 5/2012 | Irion |
| 8,194,380 B2 | 6/2012 | Murata |
| 8,197,400 B2 | 6/2012 | Boutillette |
| 8,200,042 B2 | 6/2012 | Doi |
| 8,208,015 B2 | 6/2012 | Unsai |
| 8,211,009 B2 | 7/2012 | Tanaka |
| 8,212,862 B2 | 7/2012 | Kase |
| 8,212,863 B2 | 7/2012 | Tanaka |
| 8,221,309 B2 | 7/2012 | Iida |
| 8,221,311 B2 | 7/2012 | Campos |
| 8,223,198 B2 | 7/2012 | Shibasaki |
| 8,228,369 B2 | 7/2012 | Kojima |
| 8,229,549 B2 | 7/2012 | Whitman |
| 8,235,942 B2 | 8/2012 | Frassica |
| 8,248,414 B2 | 8/2012 | Gattani |
| 8,262,565 B2 | 9/2012 | Okada |
| 8,279,275 B2 | 10/2012 | Gono |
| 8,295,566 B2 | 10/2012 | Nishimura |
| 8,300,325 B2 | 10/2012 | Katahira |
| 8,310,529 B2 | 11/2012 | Krupnick |
| 8,334,900 B2 | 12/2012 | Qu |
| 8,345,092 B2 | 1/2013 | Takasaki |
| 8,348,835 B2 | 1/2013 | Fujimori |
| 8,360,960 B2 | 1/2013 | Sasaki |
| 8,360,964 B2 | 1/2013 | Ertas |
| 8,366,623 B2 | 2/2013 | Misono |
| 8,382,673 B2 | 2/2013 | Nagano |
| 8,394,013 B2 | 3/2013 | Ichimura |
| 8,394,014 B2 | 3/2013 | Fuerst |
| 8,425,405 B2 | 4/2013 | Mitani |
| 8,435,173 B2 | 5/2013 | Hosaka |
| 8,439,829 B2 | 5/2013 | Miyamoto |
| 8,444,547 B2 | 5/2013 | Miyamoto |
| 8,444,548 B2 | 5/2013 | Kumei |
| 8,449,456 B2 | 5/2013 | Ueno |
| 8,449,457 B2 | 5/2013 | Aizenfeld |
| 8,456,562 B2 | 6/2013 | Ishii |
| 8,460,182 B2 | 6/2013 | Ouyang |
| 8,465,421 B2 | 6/2013 | Finkman |
| 8,480,670 B2 | 7/2013 | Sugita |
| 8,491,467 B2 | 7/2013 | Miyamoto |
| 8,520,919 B2 | 8/2013 | Stepp |
| 8,523,764 B2 | 9/2013 | Hatcher |
| 8,523,766 B2 | 9/2013 | Kudoh |
| 2002/0007110 A1 | 1/2002 | Irion |
| 2002/0087047 A1 | 7/2002 | Remijan |
| 2002/0098732 A1 | 7/2002 | Shimizu |
| 2002/0109774 A1 * | 8/2002 | Meron et al. .................... 348/74 |
| 2002/0151768 A1 | 10/2002 | Akiba |
| 2002/0161281 A1 | 10/2002 | Jaffe |
| 2002/0161282 A1 | 10/2002 | Fulghum |
| 2002/0183591 A1 | 12/2002 | Matsuura |
| 2003/0030918 A1 | 2/2003 | Murayama |
| 2003/0032860 A1 | 2/2003 | Avni |
| 2003/0036681 A1 | 2/2003 | Aviv |
| 2003/0055314 A1 | 3/2003 | Petitto |

(56) References Cited

U.S. PATENT DOCUMENTS

| | | |
|---|---|---|
| 2003/0083552 A1 | 5/2003 | Remijan |
| 2003/0125788 A1 | 7/2003 | Long |
| 2003/0130564 A1 | 7/2003 | Martone |
| 2003/0139648 A1 | 7/2003 | Foley |
| 2003/0158462 A1 | 8/2003 | Takase |
| 2003/0181787 A1 | 9/2003 | Kondo |
| 2003/0199860 A1 | 10/2003 | Loeb |
| 2004/0015049 A1 | 1/2004 | Zaar |
| 2004/0019347 A1 | 1/2004 | Sakurai |
| 2004/0024290 A1 | 2/2004 | Root |
| 2004/0034311 A1 | 2/2004 | Mihalcik |
| 2004/0073120 A1 | 4/2004 | Motz |
| 2004/0104999 A1 | 6/2004 | Okada |
| 2004/0111012 A1 | 6/2004 | Whitman |
| 2004/0133076 A1 | 7/2004 | Kobayashi |
| 2004/0138532 A1 | 7/2004 | Glukhovsky |
| 2004/0143162 A1 | 7/2004 | Krattiger |
| 2004/0158129 A1 | 8/2004 | Okada |
| 2004/0160682 A1 | 8/2004 | Miyano |
| 2004/0176661 A1 | 9/2004 | Futatsugi |
| 2004/0190159 A1 | 9/2004 | Hasegawa |
| 2004/0210113 A1 | 10/2004 | Hasegawa |
| 2004/0220451 A1 | 11/2004 | Gravenstein |
| 2004/0242958 A1 | 12/2004 | Fujikawa |
| 2004/0242961 A1 | 12/2004 | Bughici |
| 2004/0249247 A1 | 12/2004 | Iddan |
| 2004/0254423 A1 | 12/2004 | Wendlandt |
| 2004/0267093 A1 | 12/2004 | Miyagi |
| 2005/0020876 A1 | 1/2005 | Shioda |
| 2005/0027164 A1 | 2/2005 | Barbato |
| 2005/0038317 A1 | 2/2005 | Ratnakar |
| 2005/0038318 A1 | 2/2005 | Goldwasser |
| 2005/0043583 A1 | 2/2005 | Killmann |
| 2005/0080342 A1 | 4/2005 | Gilreath |
| 2005/0090709 A1 | 4/2005 | Okada |
| 2005/0096501 A1 | 5/2005 | Stelzer |
| 2005/0154255 A1 | 7/2005 | Jacobs |
| 2005/0154262 A1 | 7/2005 | Banik |
| 2005/0182295 A1 | 8/2005 | Soper |
| 2005/0203338 A1 | 9/2005 | Couvillon |
| 2005/0234296 A1 | 10/2005 | Saadat |
| 2005/0234347 A1 | 10/2005 | Yamataka |
| 2005/0251127 A1 | 11/2005 | Brosch |
| 2005/0256376 A1 | 11/2005 | Bar-Or |
| 2005/0261553 A1 | 11/2005 | Swain |
| 2005/0272975 A1 | 12/2005 | McWeeney |
| 2005/0283048 A1 | 12/2005 | Gill |
| 2005/0284491 A1 | 12/2005 | Tashiro |
| 2006/0047184 A1 | 3/2006 | Banik |
| 2006/0052663 A1 | 3/2006 | Koitabashi |
| 2006/0063976 A1 | 3/2006 | Aizenfeld |
| 2006/0069307 A1 | 3/2006 | Boulais |
| 2006/0069314 A1 | 3/2006 | Farr |
| 2006/0149129 A1 | 7/2006 | Watts |
| 2006/0173244 A1 | 8/2006 | Boulais |
| 2006/0183971 A1 | 8/2006 | Haviv |
| 2006/0183975 A1 | 8/2006 | Saadat |
| 2006/0189845 A1 | 8/2006 | Maahs |
| 2006/0211916 A1 | 9/2006 | Kasahara |
| 2006/0217594 A1 | 9/2006 | Ferguson |
| 2006/0224040 A1 | 10/2006 | Khait |
| 2006/0229499 A1 | 10/2006 | Eisenkolb |
| 2006/0241347 A1 | 10/2006 | Whitehead |
| 2006/0252994 A1 | 11/2006 | Ratnakar |
| 2006/0264704 A1* | 11/2006 | Fujimori et al. ............ 600/101 |
| 2006/0293556 A1 | 12/2006 | Garner |
| 2006/0293562 A1 | 12/2006 | Uchimura |
| 2007/0015964 A1 | 1/2007 | Eversull |
| 2007/0015968 A1 | 1/2007 | Shelnutt |
| 2007/0019916 A1 | 1/2007 | Takami |
| 2007/0020694 A1 | 1/2007 | Pickford |
| 2007/0030345 A1 | 2/2007 | Amling |
| 2007/0049803 A1 | 3/2007 | Moriyama |
| 2007/0055100 A1 | 3/2007 | Kato |
| 2007/0073109 A1 | 3/2007 | Irion |
| 2007/0078304 A1 | 4/2007 | Shimizu |
| 2007/0083081 A1 | 4/2007 | Schlagenhauf |
| 2007/0100206 A1 | 5/2007 | Lin |
| 2007/0106119 A1 | 5/2007 | Hirata |
| 2007/0115376 A1 | 5/2007 | Igarashi |
| 2007/0118019 A1 | 5/2007 | Mitani |
| 2007/0123748 A1 | 5/2007 | Meglan |
| 2007/0142711 A1 | 6/2007 | Bayer |
| 2007/0162095 A1 | 7/2007 | Kimmel |
| 2007/0167673 A1 | 7/2007 | Enomoto |
| 2007/0167681 A1 | 7/2007 | Gill |
| 2007/0173686 A1 | 7/2007 | Lin |
| 2007/0173687 A1 | 7/2007 | Shima |
| 2007/0177008 A1 | 8/2007 | Bayer |
| 2007/0177009 A1 | 8/2007 | Bayer |
| 2007/0185384 A1 | 8/2007 | Bayer |
| 2007/0197875 A1 | 8/2007 | Osaka |
| 2007/0203396 A1 | 8/2007 | McCutcheon |
| 2007/0206945 A1 | 9/2007 | DeLorme |
| 2007/0208225 A1 | 9/2007 | Czaniera |
| 2007/0213590 A1 | 9/2007 | Squicciarini |
| 2007/0213591 A1 | 9/2007 | Aizenfeld |
| 2007/0225556 A1 | 9/2007 | Ortiz |
| 2007/0225565 A1 | 9/2007 | Ogino |
| 2007/0229656 A1* | 10/2007 | Khait et al. ................. 348/77 |
| 2007/0244353 A1 | 10/2007 | Larsen |
| 2007/0244362 A1 | 10/2007 | El-Hachem |
| 2007/0244366 A1 | 10/2007 | Murata |
| 2007/0249899 A1 | 10/2007 | Seifert |
| 2007/0265498 A1 | 11/2007 | Ito |
| 2007/0282165 A1 | 12/2007 | Hopkins |
| 2007/0293720 A1 | 12/2007 | Bayer |
| 2008/0009672 A1 | 1/2008 | Krattiger |
| 2008/0021274 A1 | 1/2008 | Bayer |
| 2008/0021281 A1 | 1/2008 | Fujimori |
| 2008/0039689 A1 | 2/2008 | Yoshimitsu |
| 2008/0039693 A1 | 2/2008 | Karasawa |
| 2008/0045797 A1* | 2/2008 | Yasushi et al. ............ 600/175 |
| 2008/0051628 A1 | 2/2008 | Pecherer |
| 2008/0051629 A1 | 2/2008 | Sugiyama |
| 2008/0051655 A1 | 2/2008 | Sato |
| 2008/0058595 A1 | 3/2008 | Snoke |
| 2008/0058598 A1 | 3/2008 | Ries |
| 2008/0058601 A1* | 3/2008 | Fujimori ..................... 600/167 |
| 2008/0064931 A1 | 3/2008 | Schena |
| 2008/0065127 A1 | 3/2008 | Adams |
| 2008/0071290 A1 | 3/2008 | Larkin |
| 2008/0100699 A1 | 5/2008 | Hibi |
| 2008/0130108 A1 | 6/2008 | Bayer |
| 2008/0139881 A1 | 6/2008 | Cover |
| 2008/0167529 A1* | 7/2008 | Otawara ..................... 600/168 |
| 2008/0171910 A1 | 7/2008 | Kanazawa |
| 2008/0177139 A1 | 7/2008 | Courtney |
| 2008/0177140 A1 | 7/2008 | Cline |
| 2008/0188715 A1 | 8/2008 | Fujimoto |
| 2008/0225134 A1 | 9/2008 | Amling |
| 2008/0255425 A1 | 10/2008 | Voegele |
| 2008/0262302 A1 | 10/2008 | Azarbarzin |
| 2008/0262312 A1 | 10/2008 | Carroll |
| 2008/0312497 A1 | 12/2008 | Elmouelhi |
| 2009/0054790 A1 | 2/2009 | Czaniera |
| 2009/0062615 A1 | 3/2009 | Yamaya |
| 2009/0086017 A1 | 4/2009 | Miyano |
| 2009/0093679 A1 | 4/2009 | Suigetsu |
| 2009/0118577 A9 | 5/2009 | Snay |
| 2009/0137869 A1 | 5/2009 | Soutorine |
| 2009/0147076 A1 | 6/2009 | Ertas |
| 2009/0161234 A1 | 6/2009 | Sasamoto |
| 2009/0163769 A1 | 6/2009 | Robertson |
| 2009/0209811 A1 | 8/2009 | Higuchi |
| 2009/0216084 A1 | 8/2009 | Yamane |
| 2009/0231419 A1 | 9/2009 | Bayer |
| 2009/0247831 A1 | 10/2009 | Miyamoto |
| 2009/0253966 A1 | 10/2009 | Ichimura |
| 2009/0259097 A1 | 10/2009 | Thompson |
| 2009/0259102 A1 | 10/2009 | Koninckx |
| 2009/0268011 A1 | 10/2009 | Scott |
| 2009/0284649 A1 | 11/2009 | Pease |
| 2009/0287047 A1 | 11/2009 | Onoda |

(56) References Cited

U.S. PATENT DOCUMENTS

| | | |
|---|---|---|
| 2009/0287192 A1 | 11/2009 | Vivenzio |
| 2009/0290236 A1 | 11/2009 | Wang |
| 2009/0299144 A1* | 12/2009 | Shigemori ......... A61B 1/00016 600/160 |
| 2009/0306474 A1 | 12/2009 | Wilson |
| 2009/0306476 A1 | 12/2009 | Banik |
| 2009/0318757 A1 | 12/2009 | Singh |
| 2010/0010301 A1 | 1/2010 | Hale |
| 2010/0010302 A1 | 1/2010 | Hadani |
| 2010/0013914 A1 | 1/2010 | Bettesh |
| 2010/0016673 A1 | 1/2010 | Bandy |
| 2010/0030020 A1 | 2/2010 | Sanders |
| 2010/0042097 A1 | 2/2010 | Newton |
| 2010/0047733 A1 | 2/2010 | Nahlieli |
| 2010/0053312 A1 | 3/2010 | Watanabe |
| 2010/0073470 A1 | 3/2010 | Takasaki |
| 2010/0076268 A1 | 3/2010 | Takasugi |
| 2010/0081874 A1 | 4/2010 | Miyamoto |
| 2010/0081875 A1 | 4/2010 | Fowler |
| 2010/0087706 A1 | 4/2010 | Syed |
| 2010/0121142 A1 | 5/2010 | Ouyang |
| 2010/0123950 A1 | 5/2010 | Fujiwara |
| 2010/0130822 A1* | 5/2010 | Katayama et al. ............ 600/118 |
| 2010/0137682 A1 | 6/2010 | Doguchi |
| 2010/0137687 A1 | 6/2010 | Schwartz |
| 2010/0141746 A1 | 6/2010 | Ikeda |
| 2010/0152612 A1 | 6/2010 | Headley |
| 2010/0160729 A1 | 6/2010 | Smith |
| 2010/0174144 A1 | 7/2010 | Hsu |
| 2010/0185056 A1 | 7/2010 | Gordon |
| 2010/0187408 A1 | 7/2010 | Klem |
| 2010/0201985 A1 | 8/2010 | Wang |
| 2010/0204609 A1 | 8/2010 | Worth |
| 2010/0217076 A1 | 8/2010 | Ratnakar |
| 2010/0217081 A1 | 8/2010 | Deppmeier |
| 2010/0228086 A1 | 9/2010 | Ohki |
| 2010/0245653 A1 | 9/2010 | Bodor |
| 2010/0249496 A1 | 9/2010 | Cardenas |
| 2010/0256447 A1 | 10/2010 | Dubi |
| 2010/0286475 A1 | 11/2010 | Robertson |
| 2010/0296178 A1 | 11/2010 | Genet |
| 2010/0298640 A1 | 11/2010 | Oneda |
| 2010/0298773 A1 | 11/2010 | Nitsan |
| 2010/0305503 A1 | 12/2010 | Fang |
| 2010/0317919 A1 | 12/2010 | Takaoka |
| 2010/0317921 A1 | 12/2010 | Marple |
| 2010/0318061 A1 | 12/2010 | Derrick |
| 2011/0028790 A1 | 2/2011 | Farr |
| 2011/0054256 A1 | 3/2011 | Cushner |
| 2011/0112363 A1 | 5/2011 | Koga |
| 2011/0160530 A1 | 6/2011 | Ratnakar |
| 2011/0169931 A1 | 7/2011 | Pascal |
| 2011/0184243 A1 | 7/2011 | Wright |
| 2011/0196200 A1 | 8/2011 | Glozman |
| 2011/0196204 A1 | 8/2011 | Setty |
| 2011/0211267 A1 | 9/2011 | Takato |
| 2011/0224487 A1 | 9/2011 | Ogawa |
| 2011/0245600 A1 | 10/2011 | Ishii |
| 2011/0245609 A1 | 10/2011 | Laser |
| 2011/0257478 A1 | 10/2011 | Kleiner |
| 2011/0263938 A1 | 10/2011 | Levy |
| 2011/0282144 A1* | 11/2011 | Gettman ................. 600/109 |
| 2011/0282148 A1 | 11/2011 | Kase |
| 2011/0288374 A1 | 11/2011 | Hadani |
| 2011/0295061 A1 | 12/2011 | Haramaty |
| 2011/0295062 A1 | 12/2011 | GratacosSolsona |
| 2011/0295064 A1 | 12/2011 | Kagawa |
| 2011/0306832 A1 | 12/2011 | Bassan |
| 2011/0313249 A1 | 12/2011 | Viola |
| 2012/0010465 A1 | 1/2012 | Erikawa |
| 2012/0029291 A1 | 2/2012 | Wallace |
| 2012/0040305 A1 | 2/2012 | Karazivan |
| 2012/0041534 A1 | 2/2012 | Clerc |
| 2012/0046524 A1 | 2/2012 | Miyamoto |
| 2012/0053407 A1 | 3/2012 | Levy |
| 2012/0057251 A1 | 3/2012 | Takato |
| 2012/0065468 A1 | 3/2012 | Levy |
| 2012/0071748 A1 | 3/2012 | Mark |
| 2012/0078042 A1 | 3/2012 | Uram |
| 2012/0088965 A1 | 4/2012 | Stokes |
| 2012/0095391 A1 | 4/2012 | Bendele |
| 2012/0104230 A1 | 5/2012 | Eismann |
| 2012/0178995 A1 | 7/2012 | Newton |
| 2012/0209062 A1 | 8/2012 | Qiao |
| 2012/0229615 A1 | 9/2012 | Kirma |
| 2012/0232340 A1 | 9/2012 | Levy |
| 2012/0232342 A1 | 9/2012 | Reydel |
| 2012/0232343 A1 | 9/2012 | Levy |
| 2012/0253121 A1* | 10/2012 | Kitano ........................ 600/109 |
| 2012/0253284 A1 | 10/2012 | Nitsan |
| 2012/0259175 A1 | 10/2012 | Reydel |
| 2012/0265094 A1 | 10/2012 | Goldfarb |
| 2013/0012778 A1 | 1/2013 | Bayer |
| 2013/0012794 A1 | 1/2013 | Zeng |
| 2013/0060086 A1 | 3/2013 | Talbert |
| 2013/0109916 A1 | 5/2013 | Levy |
| 2013/0109918 A1 | 5/2013 | Pagan |
| 2013/0110003 A1 | 5/2013 | Surti |
| 2013/0131445 A1 | 5/2013 | Zerfas |
| 2013/0131447 A1 | 5/2013 | Benning |
| 2013/0131454 A1 | 5/2013 | McCormack |
| 2013/0137930 A1 | 5/2013 | Menabde |
| 2013/0172670 A1 | 7/2013 | Levy |
| 2013/0172673 A1 | 7/2013 | Kennedy |
| 2013/0172674 A1 | 7/2013 | Kennedy |
| 2013/0172677 A1 | 7/2013 | Kennedy |
| 2013/0172678 A1 | 7/2013 | Kennedy |
| 2013/0190561 A1 | 7/2013 | Oskin |
| 2013/0194404 A1 | 8/2013 | Christiansen |
| 2013/0204088 A1 | 8/2013 | Miyamoto |
| 2013/0296649 A1 | 11/2013 | Kirma |
| 2013/0314521 A1 | 11/2013 | Satake |
| 2013/0317295 A1 | 11/2013 | Morse |
| 2014/0364691 A1 | 12/2014 | Krivopisk |

FOREIGN PATENT DOCUMENTS

| | | |
|---|---|---|
| CN | 201108422 Y | 9/2008 |
| CN | 101396258 | 4/2009 |
| CN | 102058375 A | 5/2011 |
| CN | 102058380 A | 5/2011 |
| CN | 101061940 | 6/2011 |
| CN | 201870615 U | 6/2011 |
| DE | 102005008153 A1 | 11/2005 |
| EP | 0029555 A2 | 6/1981 |
| EP | 543738 A1 | 5/1993 |
| EP | 730844 | 9/1996 |
| EP | 1195630 A2 | 4/2002 |
| EP | 1325458 | 7/2003 |
| EP | 1347702 A2 | 10/2003 |
| EP | 948283 B1 | 4/2004 |
| EP | 1535565 | 6/2005 |
| EP | 1073365 B1 | 7/2005 |
| EP | 1627595 A1 | 2/2006 |
| EP | 668738 B1 | 6/2006 |
| EP | 1685790 | 8/2006 |
| EP | 1685790 A1 | 8/2006 |
| EP | 1472972 B1 | 10/2006 |
| EP | 1790280 A1 | 5/2007 |
| EP | 1834572 A1 | 9/2007 |
| EP | 1952750 | 8/2008 |
| EP | 1977675 | 10/2008 |
| EP | 1977682 A2 | 10/2008 |
| EP | 1974000653 | 10/2008 |
| EP | 1992292 A1 | 11/2008 |
| EP | 2022389 A1 | 2/2009 |
| EP | 2144571 A2 | 1/2010 |
| EP | 2276389 A1 | 1/2011 |
| EP | 1835847 B1 | 5/2011 |
| EP | 1870014 B1 | 1/2012 |
| EP | 2501271 A1 | 9/2012 |
| EP | 2503933 A1 | 10/2012 |
| EP | 2512577 A2 | 10/2012 |
| EP | 2529660 A1 | 12/2012 |

(56) References Cited

FOREIGN PATENT DOCUMENTS

| | | |
|---|---|---|
| EP | 2596756 A1 | 5/2013 |
| EP | 2623019 A1 | 8/2013 |
| GB | 2321132 | 7/1998 |
| GB | 2352922 A | 2/2001 |
| JP | 55078932 | 6/1980 |
| JP | 61055657 | 11/1986 |
| JP | H02188709 A | 7/1990 |
| JP | 5049000594 | 3/1993 |
| JP | H05309069 | 11/1993 |
| JP | 6105000800 | 4/1994 |
| JP | 7000000352 | 1/1995 |
| JP | 8122000657 | 5/1996 |
| JP | 1013007179 | 4/1998 |
| JP | 1015001113 | 6/1998 |
| JP | 11137512 | 5/1999 |
| JP | H11125773 | 5/1999 |
| JP | H11125773 A | 5/1999 |
| JP | 1116009340 | 6/1999 |
| JP | 1116009341 | 6/1999 |
| JP | H11253401 | 9/1999 |
| JP | 2000171727 A | 6/2000 |
| JP | 2000330015 A | 11/2000 |
| JP | 2001061762 | 3/2001 |
| JP | 2001198086 | 7/2001 |
| JP | 2002000559 | 1/2002 |
| JP | 2002017667 | 1/2002 |
| JP | 2002058636 | 2/2002 |
| JP | 200265589 A | 3/2002 |
| JP | 2002065575 | 3/2002 |
| JP | 2002078675 | 3/2002 |
| JP | 2002216902 | 8/2002 |
| JP | 2002291693 | 10/2002 |
| JP | 2003038431 | 2/2003 |
| JP | 2003061900 | 3/2003 |
| JP | 2003111724 | 4/2003 |
| JP | 2003190082 | 7/2003 |
| JP | 2003220017 | 8/2003 |
| JP | 2003245247 | 9/2003 |
| JP | 2004022391 | 1/2004 |
| JP | 2004049754 | 2/2004 |
| JP | 2004049756 | 2/2004 |
| JP | 2004129834 | 4/2004 |
| JP | 2004205779 A | 7/2004 |
| JP | 2005013557 A | 1/2005 |
| JP | 2005058547 | 3/2005 |
| JP | 2005253543 | 9/2005 |
| JP | 2005323874 A | 11/2005 |
| JP | 3765500 | 2/2006 |
| JP | 2006068109 A | 3/2006 |
| JP | 2006218155 | 8/2006 |
| JP | 2006280954 | 10/2006 |
| JP | 2006288758 | 10/2006 |
| JP | 2007020866 A | 2/2007 |
| JP | 2007185276 | 7/2007 |
| JP | 2008068025 | 3/2008 |
| JP | 2008118568 | 5/2008 |
| JP | 2008161569 A | 7/2008 |
| JP | 2008229204 | 10/2008 |
| JP | 2008257108 A | 10/2008 |
| JP | 2009233186 | 10/2009 |
| JP | 4445647 | 4/2010 |
| JP | 2010178766 A | 8/2010 |
| JP | 2010279539 | 12/2010 |
| WO | 9219148 A1 | 11/1992 |
| WO | 0052643 A1 | 9/2000 |
| WO | 0245595 | 6/2002 |
| WO | 2004026125 | 4/2004 |
| WO | 2005082228 A1 | 9/2005 |
| WO | 2006073581 | 7/2006 |
| WO | 2006105932 A1 | 10/2006 |
| WO | 2007087421 | 8/2007 |
| WO | 2007113801 | 10/2007 |
| WO | 2007113801 A2 | 10/2007 |
| WO | 2007136859 A2 | 11/2007 |
| WO | 2008012813 A1 | 1/2008 |
| WO | 2008073243 | 6/2008 |
| WO | 2008093288 | 8/2008 |
| WO | 2008139770 | 11/2008 |
| WO | 2008155776 | 12/2008 |
| WO | 2008156623 | 12/2008 |
| WO | 2009009414 | 1/2009 |
| WO | 2009025843 | 2/2009 |
| WO | 2009040744 | 4/2009 |
| WO | 2009095915 | 8/2009 |
| WO | 2010028612 | 3/2010 |
| WO | 2010045406 | 4/2010 |
| WO | 2010064506 | 6/2010 |
| WO | 2010066788 | 6/2010 |
| WO | 2010146587 | 12/2010 |
| WO | 2010146587 A1 | 12/2010 |
| WO | 2011008922 | 1/2011 |
| WO | 2011041724 | 4/2011 |
| WO | 2011083451 | 7/2011 |
| WO | 2011126812 | 10/2011 |
| WO | 2012038958 | 3/2012 |
| WO | 2012056453 | 5/2012 |
| WO | 2012077116 | 6/2012 |
| WO | 2012077117 | 6/2012 |
| WO | 2012088201 A2 | 6/2012 |
| WO | 2012103266 | 8/2012 |
| WO | 2012120507 | 9/2012 |
| WO | 2012153324 | 11/2012 |
| WO | 2013014673 | 1/2013 |
| WO | 2013024476 | 2/2013 |
| WO | 2013043704 | 3/2013 |
| WO | 2013128136 | 9/2013 |

OTHER PUBLICATIONS

Office Action dated May 27, 2014 for U.S. Appl. No. 13/212,627.
Brochure for US Endoscopy's AquaShield Water Bottle System, 2010.
First Image of an Endo Smart Cap, made by Medivators, and obtained from http://www.bymemedical.com/prod/145L.jpg and advertised at http://www.medivators.com/products/endoscopy-procedure-products/irrigation-tubing/endo-smartcap%C2%AE.
International Search Report for PCT/EP2009/066726, Aug. 16, 2010.
International Search Report for PCT/IL2011/000832, May 16, 2012.
International Search Report for PCT/IL2011/050049, May 15, 2012.
International Search Report for PCT/IL2011/050050, May 16, 2012.
International Search Report for PCT/IL2012/050037, Jun. 1, 2012.
International Search Report for PCT/IL2012/050274, Nov. 15, 2012.
International Search Report for PCT/IL2012/050299, Nov. 15, 2012.
International Search Report for PCT/IL2013/050840, Feb. 2, 2014.
International Search Report of PCT/IL10/00476 mailed Sep. 27, 2010, 2 pages.
International Search Report of PCT/IL2011/000745, dated May 8, 2012.
Office Action dated Apr. 3, 2014 for U.S. Appl. No. 13/413,141.
Office Action dated Feb. 24, 2014 for U.S. Appl. No. 13/190,968.
Office Action dated Feb. 27, 2014 for U.S. Appl. No. 13/557,114.
Office Action dated Jul. 1, 2014 for U.S. Appl. No. 13/655,120.
Office Action dated Jul. 31, 2014 for U.S. Appl. No. 13/713,449.
Office Action dated Jun. 12, 2014 for U.S. Appl. No. 13/713,466.
Office Action dated Mar. 28, 2014 for U.S. Appl. No. 13/413,252.
Second Image of an Endo Smart Cap, made by Medivators, and obtained from http://www.bymemedical.com/prod/150L.jpg and advertised at http://www.medivators.com/products/endoscopy-procedure-products/irrigation-tubing/endo-smartcap%C2%AE.
First Office Action for CN 2012800368972, Jun. 1, 2015.
Office Action for Chinese Patent Application No. CN2012800368972, Jan. 27, 2016.
Office Action dated Aug. 4, 2015 for U.S. Appl. No. 13/557,114.
Office Action dated Nov. 16, 2015 for U.S. Appl. No. 13/557,114.
Examination Report for Canadian Patent Application No. CA2765559, Jan. 18, 2016.
Supplementary European Search Report for EP118471911, Jan. 16, 2015.
Office Action for Chinese Patent Application No. 201280038808.8, May 20, 2015.
Extended European Search Report for EP12817452.1, Mar. 9, 2015.

(56) References Cited

OTHER PUBLICATIONS

Office Action dated Nov. 26, 2014 for U.S. Appl. No. 13/713,466.
Office Action dated Aug. 19, 2015 for U.S. Appl. No. 13/713,466.
Office Action dated Jul. 21, 2015 for U.S. Appl. No. 13/992,021.
Office Action dated Aug. 5, 2015 for U.S. Appl. No. 13/212,627.
Office Action for Chinese Patent Application No. 201180067259.2, May 29, 2015.
Office Action dated Aug. 6, 2015 for U.S. Appl. No. 13/119,032.
Office Action dated Aug. 27, 2015 for U.S. Appl. No. 13/655,120.
Office Action dated May 1, 2015 for U.S. Appl. No. 13/992,021.
Office Action dated Jun. 3, 2015 for U.S. Appl. No. 13/992,014.
Office Action dated Feb. 17, 2015 for U.S. Appl. No. 13/882,004.
Office Action dated Mar. 12, 2015 for U.S. Appl. No. 13/822,908.
First Office Action for CN 2012800171292, dated Feb. 28, 2015.
Office Action dated Jan. 15, 2015 for U.S. Appl. No. 13/190,968.
Office Action dated Aug. 18, 2015 for U.S. Appl. No. 13/713,449.
Office Action dated Feb. 13, 2015 for U.S. Appl. No. 13/713,449.
First office action for CN2011800627366, Feb. 25, 2015.
Notice of Allowance dated Jun. 8, 2015 for U.S. Appl. No. 13/984,028.
Notice of Allowance dated Jun. 8, 2015 for U.S. Appl. No. 13/413,252.
Prosecution File History for U.S. Appl. No. 13/190,968; Jul. 26, 2011 through Jun. 17, 2015.
Notice of Allowance dated Jun. 17, 2015 for U.S. Appl. No. 13/190,968.
Supplementary European Search Report for European Application No. EP12823972, May 13, 2015.
Extended European Search Report for EP14186113.8, Apr. 1, 2015.
Corrected European Search Opinion for EP14186113.8, Apr. 29, 2015.
Notice of Allowance dated Dec. 15, 2014 for U.S. Appl. No. 13/713,466.
Notice of Allowance dated Dec. 15, 2015 for U.S. Appl. No. 13/713,466.
Office Action dated Jan. 12, 2016 for U.S. Appl. No. 13/713,466.
Office Action for Japanese Patent Application No. 2013-542668, Oct. 1, 2015.
Office Action for Japanese Patent Application No. 2013-535586, Sep. 24, 2015.
Second office action for Chinese Patent Application No. 201180062736.6, Oct. 12, 2015.
Notice of Allowance dated Dec. 23, 2015 for U.S. Appl. No. 13/992,021.
Office Action dated Dec. 4, 2015 for U.S. Appl. No. 13/822,908.
Office Action dated Nov. 3, 2015 for U.S. Appl. No. 13/992,014.
Office Action dated Oct. 7, 2015 for U.S. Appl. No. 13/882,004.
Extended European Search Report for EP11846069.0, Apr. 24, 2014.

* cited by examiner

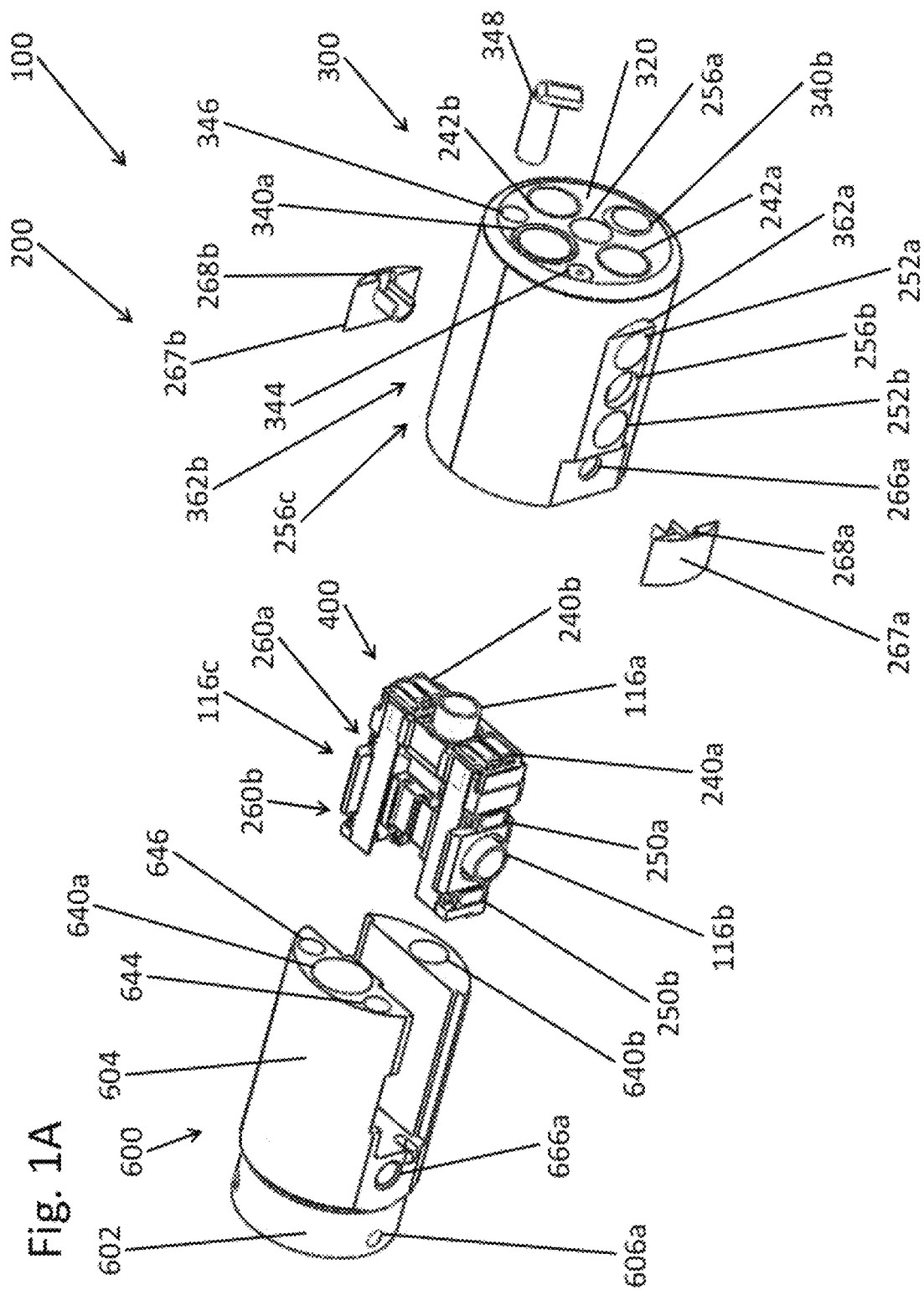

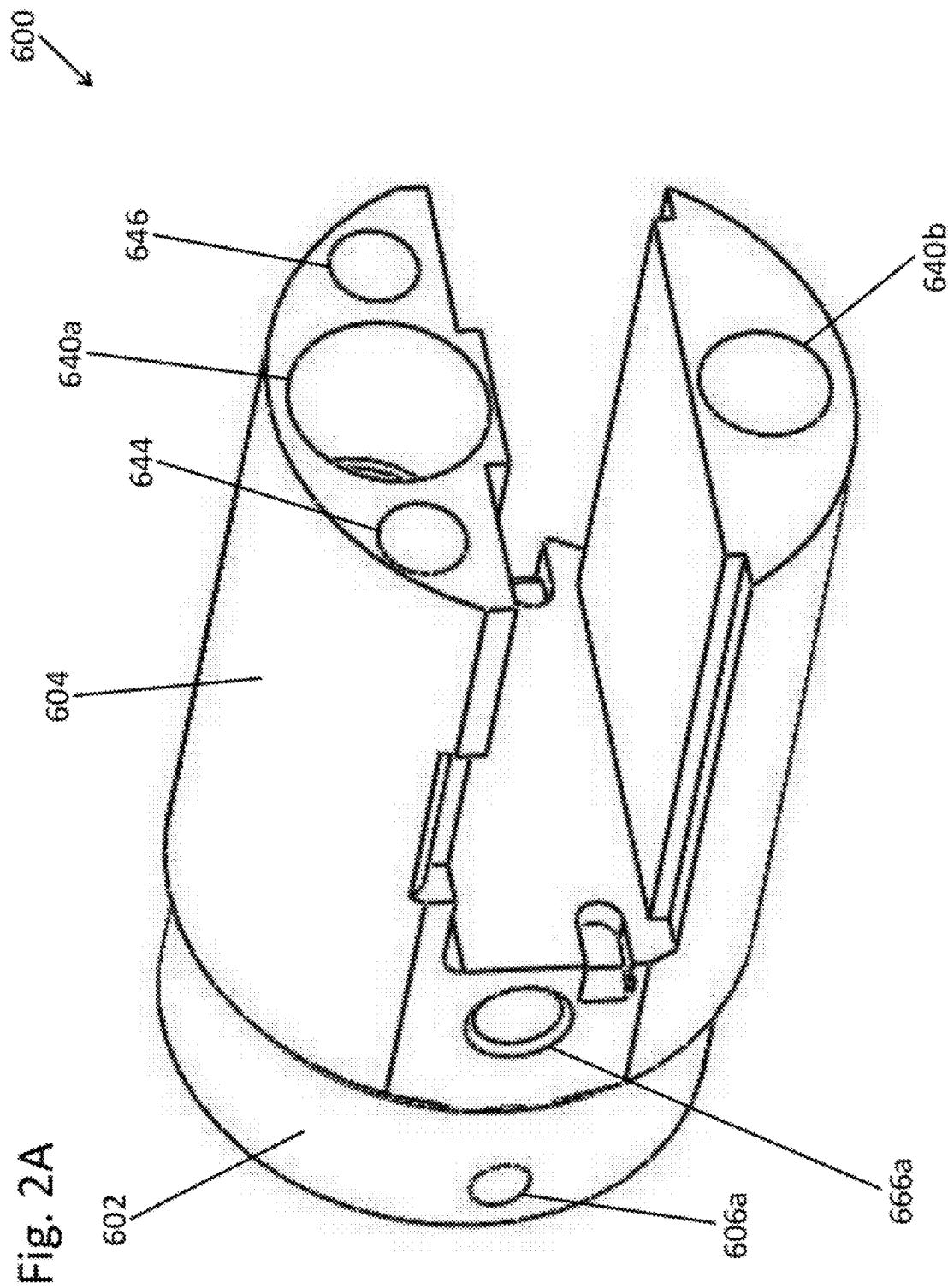

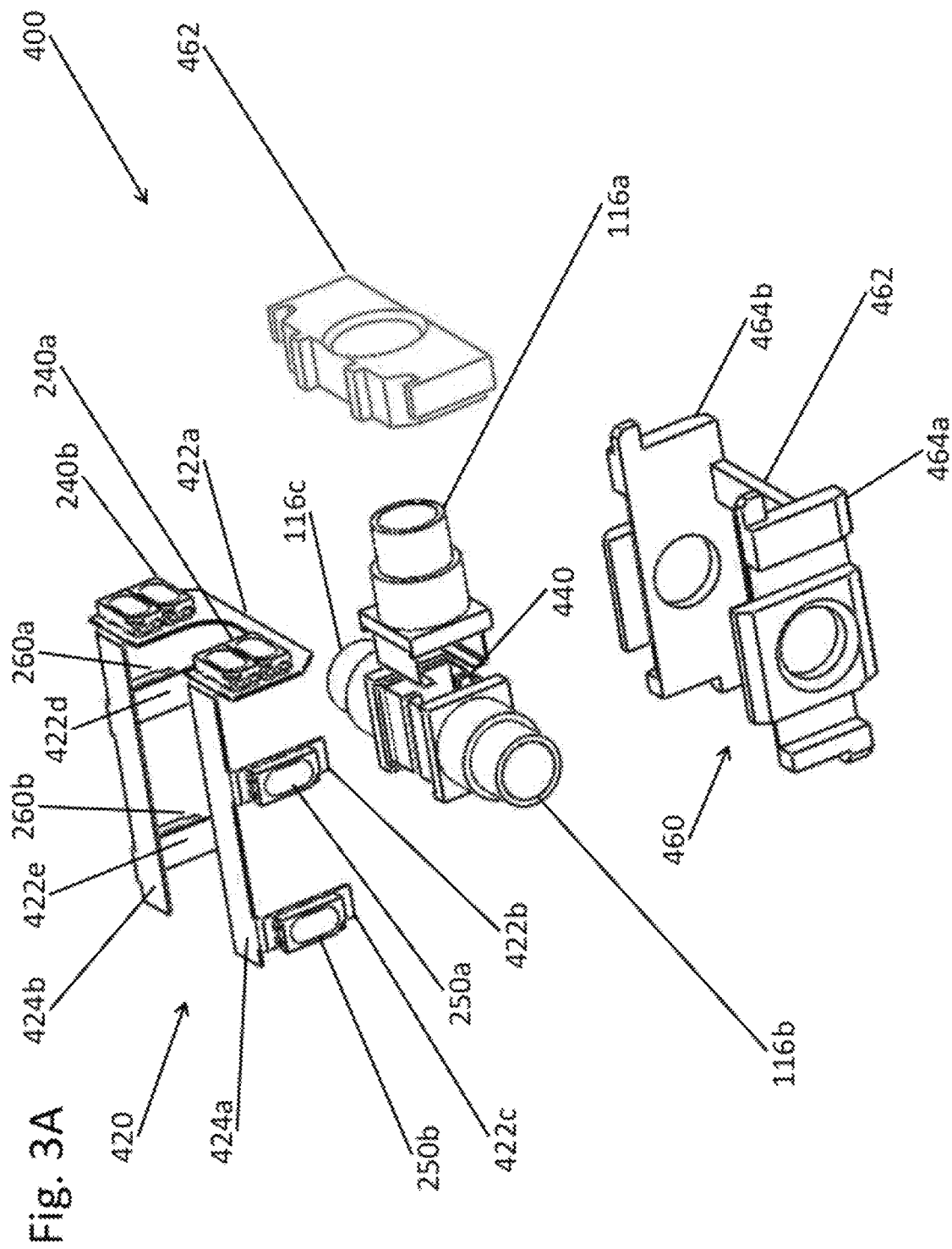

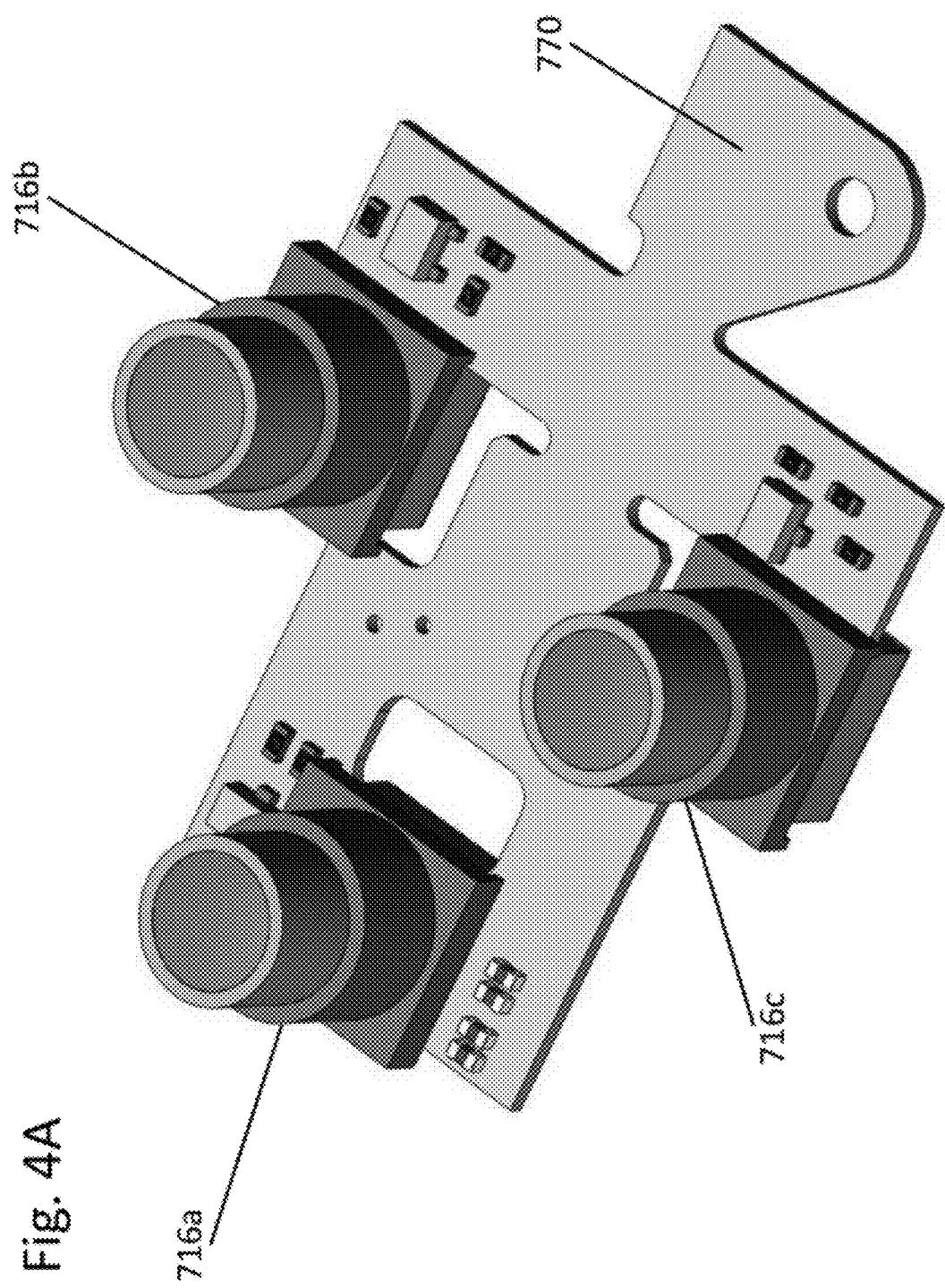

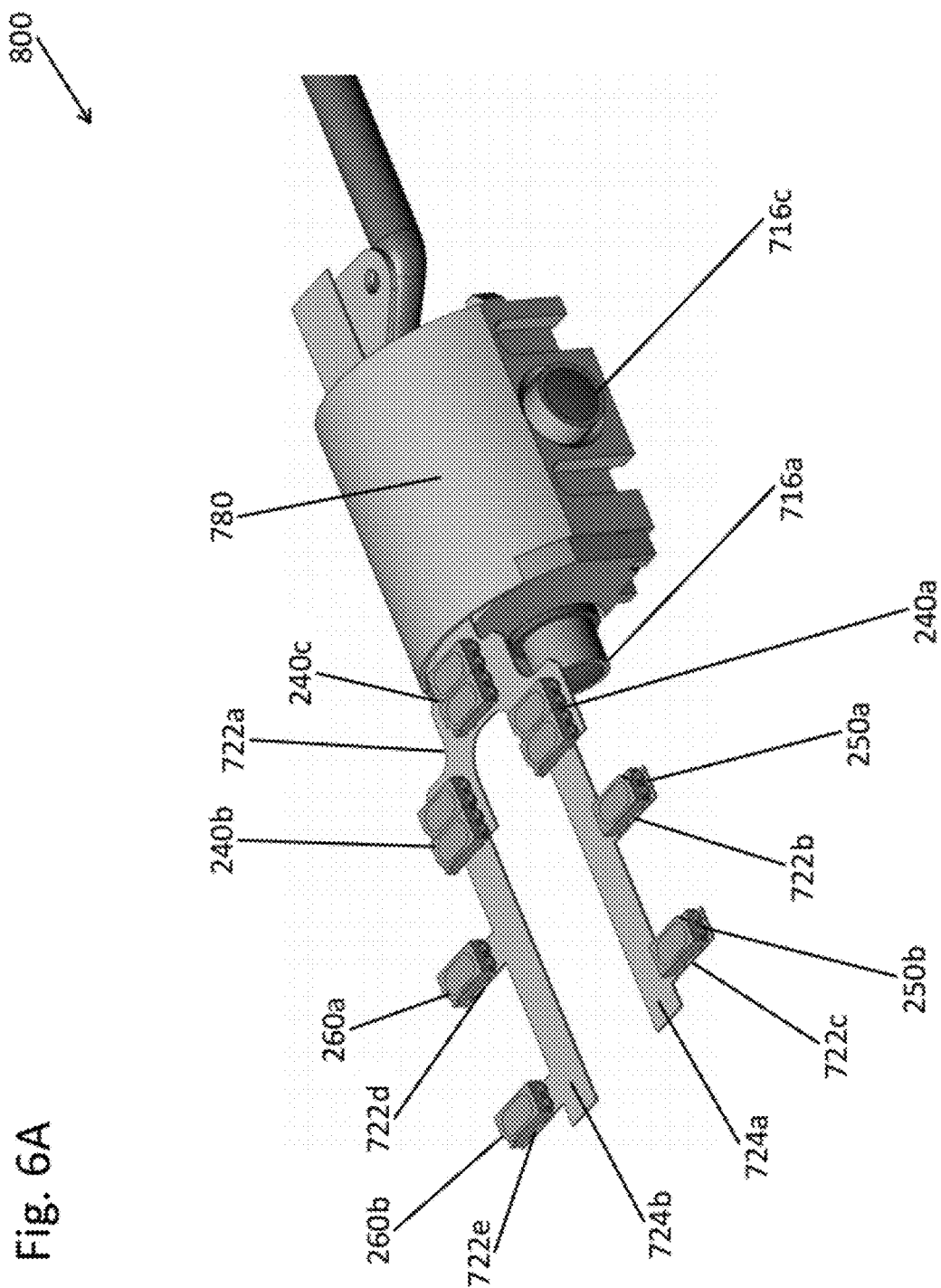

ENDOSCOPE CIRCUIT BOARD ASSEMBLY

REFERENCE TO CO-PENDING APPLICATIONS

Priority is claimed to U.S. Provisional Patent application Ser. No. 61/449,741, filed on Mar. 7, 2011.

FIELD OF THE INVENTION

Embodiments of the invention relate to an endoscope circuit board assembly.

BACKGROUND

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the body's natural orifices or through an incision in the skin.

An endoscope is usually an elongated tubular shaft, rigid or flexible, having a video camera or a fiber optic lens assembly at its distal end. The shaft is connected to a handle, which sometimes includes an ocular for direct viewing. Viewing is also usually possible via an external screen. Various surgical tools may be inserted through a working channel in the endoscope for performing different surgical procedures.

Endoscopes, such as colonoscopes, that are currently being used, typically have a front camera for viewing the internal organ, such as the colon, an illuminator, a fluid injector for cleaning the camera lens and sometimes also the illuminator and a working channel for insertion of surgical tools, for example, for removing polyps found in the colon. Often, endoscopes also have fluid injectors ("jet") for cleaning a body cavity, such as the colon, into which they are inserted. The illuminators commonly used are fiber optics which transmits light, generated remotely, to the endoscope tip section. The use of light-emitting diodes (LEDs) for illumination is also known.

One of the biggest challenges facing endoscope manufacturers is the need to miniaturize and pack a number of elements into the endoscope's tip in order to support large number of endoscope functions including operation of medical tools, imaging capabilities, field of view illumination, fluid injection, and other functions.

There is thus a need in the art for endoscopes, such as colonoscopies, that allow efficient packing of endoscope's internal parts, while maintaining endoscopes functions.

SUMMARY OF THE INVENTION

The following embodiments and aspects thereof are described and illustrated in conjunction with systems, tools and methods, which are meant to be exemplary and illustrative, not limiting in scope.

There is provided herein, according to some embodiments of the invention a circuit board assembly for a tip section of a multi-camera endoscope, the assembly comprising: a camera circuit board configured to carry at least one front-pointing camera and at least one side-pointing camera; a flexible illuminator circuit board comprising at least one foldable panel and configured to carry at least one front illuminator for essentially illuminating the field of view (FOV) of the front-pointing camera and at least one side illuminator for essentially illuminating the FOV of the side-pointing camera.

In some embodiments, the assembly further comprises one or more circuit board holders configured to support the flexible illuminator circuit board, the camera circuit board or both.

In some embodiments, the circuit board holder comprises at least one niche configured to accommodate at least one of the illuminators, and/or at least one of the cameras.

In some embodiments, the camera circuit board is a foldable camera circuit board. In some embodiments, the camera circuit board is configured to carry a front-pointing camera and two side-pointing cameras. In some embodiments, each of the side-pointing cameras is directed to opposing sides.

In some embodiments, each of the side-pointing cameras is essentially perpendicular to the front pointing camera surface.

There is further provided herein, according to some embodiments of the invention a tip section for a multi-camera endoscope, the tip section comprising: at least one front-pointing camera and at least one front illuminator associated therewith; at least one side-pointing camera and at least one side illuminator associated therewith; and a circuit board assembly comprising: a camera circuit board configured to carry at least one front-pointing camera and at least one side-pointing camera; and a flexible illuminator circuit board comprising at least one foldable panel and configured to carry at least one front illuminator and at least one side illuminator.

In some embodiments, the tip section further comprises fluid channeling component.

In some embodiments, the fluid channeling component comprises: at least one front fluid injector configured for cleaning at least one front-pointing camera and/or at least one of front illuminator; at least one fluid injector configured for cleaning at least one side-pointing camera and/or at least one of side illuminator; and a front working channel configured for insertion of a medical tool.

In some embodiments, the tip section comprises two side-pointing cameras. In some embodiments, each of two side-pointing cameras is directed to opposing sides.

In some embodiments, each of side-pointing cameras is essentially perpendicular to the front pointing camera surface. In some embodiments, at least one front and side illuminators comprises a discrete illuminator. In some embodiments, the discrete illuminator comprises a light-emitting diode (LED).

In some embodiments, at least one of the front and side illuminators is configured to emit white light. In some embodiments, at least one of the front and side illuminators is configured to emit ultraviolet light. In some embodiments, at least one of the front and side illuminators is configured to emit infrared light. In some embodiments, at least one of the front and side illuminators is configured to emit near-infrared light. In some embodiments, the front and side illuminators are configured to emit light in different wavelengths.

In some embodiments, the front-pointing camera and the side-pointing camera independently comprise a Charge Coupled Device (CCD) or a Complementary Metal Oxide Semiconductor (CMOS) image sensor.

In some embodiments, the front and side fluid injectors are connected to a same fluid supply channel. In some embodiments, the endoscope is a colonoscope. In some embodiments, fields of view of the front-pointing camera and side-pointing camera are at least partially overlapping.

In some embodiments, at least one of the front and side pointing cameras comprises a lens assembly providing a field of view of 90 degrees or more.

In some embodiments, at least one of the front and side pointing cameras comprises a lens assembly providing a field of view of 120 degrees or more.

In some embodiments, at least one of the front and side pointing cameras comprises a lens assembly providing a focal length of approximately 3-100 millimeters.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

FIG. 1A shows an exploded view of a tip section of an endoscope assembly according to some embodiments;

FIG. 2A shows a perspective view of a fluid channeling component of an endoscope assembly according to some embodiments;

FIG. 3A shows an exploded view of a tip section of a foldable electronic circuit board according to some embodiments;

FIG. 4A shows a perspective view of a camera circuit board according to some embodiments;

FIG. 6A shows a perspective view of a foldable electronic circuit board according to some embodiments;

DETAILED DESCRIPTION

Figure 1B:
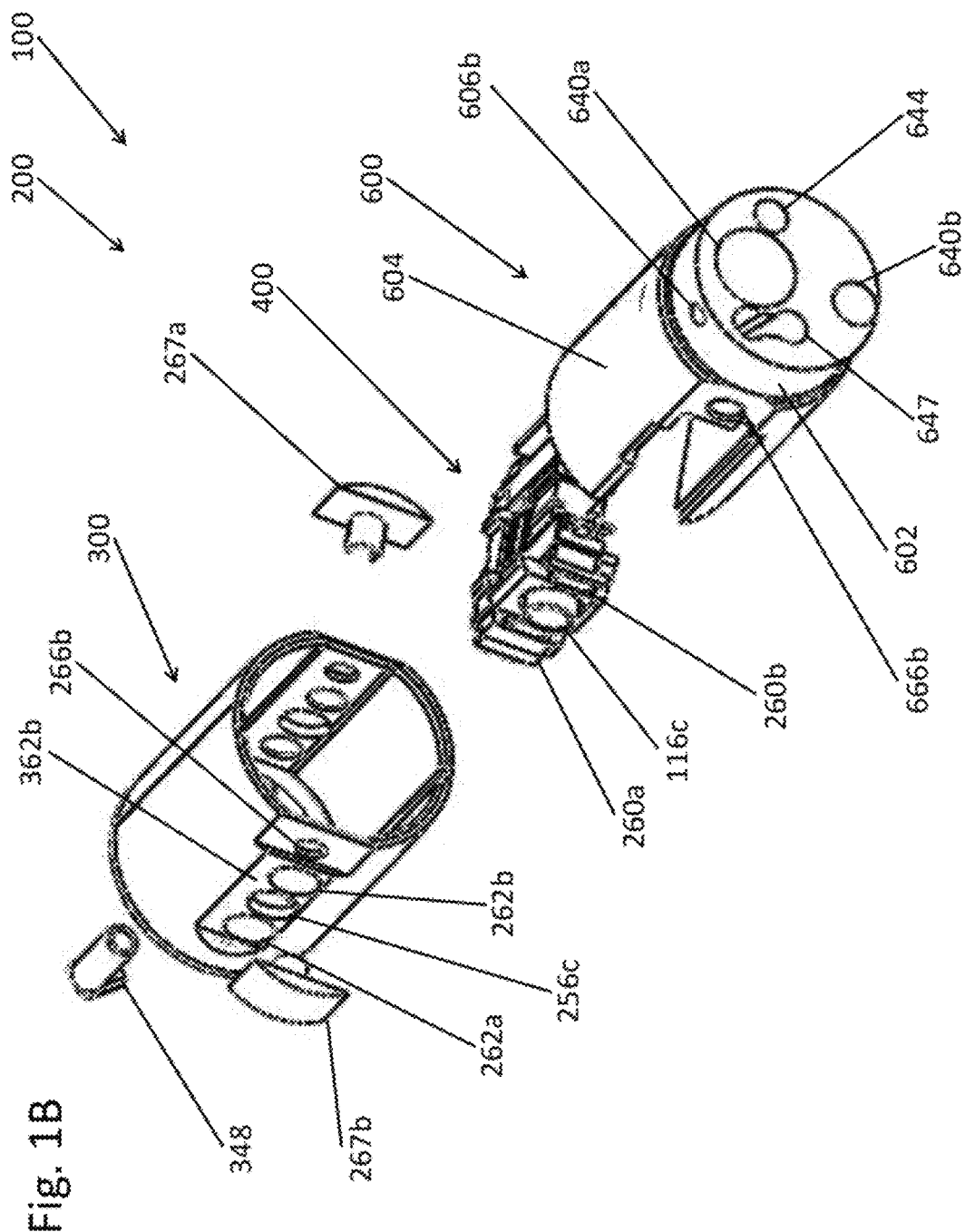
FIG. 1B shows an exploded view of a tip section of an endoscope assembly according to some embodiments.

Reference is now made to FIGS. 1A and 1B, which show exploded views of a tip section 200 of an endoscope assembly 100 according to an embodiment.

An aspect of some embodiments relates to an endoscope assembly 100 having a tip section 200 equipped with two or more front working channels.

It is noted that the term "endoscope" as mentioned to herein may refer particularly to a colonoscope, according to some embodiments, but is not limited only to colonoscopes. The term "endoscope" may refer to any instrument used to examine the interior of a hollow organ or cavity of the body.

Tip section 200 may be turnable by way of flexible shaft (not shown) which may also be referred to as a bending section, for example a vertebra mechanism.

According to some embodiments, tip section 200 of an endoscope may include a tip cover 300, a foldable electronic circuit board 400 and a fluid channeling component 600.

It is noted that the fluid channeling component (fluid channeling component 600) depicted in FIGS. 1A-2C is only a non limiting example of a possible fluid channeling component. Any fluid channeling components (such as fluid channeling component 900 depicted in FIG. 7) or any other fluid channel and/or tubing system(s) are also covered under the scope of this invention.

Tip cover 300 may be configured to fit over the inner parts of the tip section 200 including foldable electronic circuit board 400 and fluid channeling component 600 and to provide protection to the internal components in the inner parts.

Tip cover 300 may include a front panel 320 having a front optical assembly 256a of front-pointing camera 116a. Front optical assembly 256a may include a plurality of lenses, static or movable, which may provide a field of view of up to essentially 180 degrees. Front optical assembly 256a may provide a focal length of up to about 100 millimeters.

Optical axis of front-pointing camera 116a may be essentially directed along the long dimension of the endoscope. However, since front-pointing camera 116a is typically a wide angle camera, its field of view may include viewing directions at large angles to its optical axis. Additionally, front panel 320 may include optical windows 242a and 242b of illuminators 240a and 240b, respectively. It should be noted that number of illumination sources used for illumination of the field of view may vary.

In addition, front panel 320 may include a working channel opening 340a of a working channel 640a, and a second working channel opening 340b of a second working channel 640b which are further discussed below.

Jet channel opening 344 of jet channel 644 may also be located on front panel 320 of tip cover 300. Jet channel 644 may be configured for providing high-pressure jet of fluid such as water or saline for cleaning the walls of the body cavity.

Also located on front panel 320 of tip cover 300 is injector opening 346 of injector channel 646 having a nozzle 348 aimed at front optical assembly 256a.

Injector channel 646 may be fed by a fluid or fluid blend such as water and/or gas and configured for injecting fluid blend (liquid and/or gas) to wash contaminants such as blood, feces and other debris from front optical assembly 256a of front-pointing camera 116a. In addition, the fluid blend may include gas, which may be used for inflating a body cavity.

Optionally, injector channel 646 may be configured for cleaning front optical assembly 256a and one, two or all of optical windows 242a and 242b.

A sidewall 362a of tip cover 300 may include an optical assembly 256b for side-pointing camera 116b, which may be similar to front optical assembly 256a and optical windows 252a and 252b of illuminators 250a and 250b for side-pointing camera 116b.

A sidewall 362b of tip cover 300, which may be similar to sidewall 362a and located on the opposite side of tip cover 300, may include an optical assembly 256c for side-pointing camera 116c, which may be similar to front optical assembly 256a and optical windows 262a and 262b of illuminators 260a and 260b for side-pointing camera 116b.

Optical axis of side-pointing cameras 116b and 116c may be essentially directed perpendicular to the long dimension of the endoscope. However, since side-pointing cameras 116b and 116c are typically a wide angle camera, its field of view may include viewing directions at large angles to its optical axis.

According to some embodiments, side injector channels 666a and 666b may be configured to supply fluids for cleaning any of the tip elements (such as any optical assembly, windows, illuminators, and other elements). Side injectors opening 266a and 266b of side injector channels 666a and 666b may be located at distal end of sidewalls 362a and 362b respectively. Nozzle covers 267a and 267b may be configured to fit side injectors opening 266a and 266b.

Additionally, nozzle covers 267a and 267b may include nozzles 268a and 268b which may be aimed at side optical assembly 256b and 256c and configured for injecting a fluid or fluid blend to wash contaminants such as blood, feces and other debris from side optical assembly 256b and 256c of side-pointing camera 116b and 116c. Optionally, nozzles 268a and 268b may be configured for cleaning side optical assembly 256b and 256c and optical windows 252a, 252b, 262b and/or 262b.

Optionally, injector channel 646 and side injector channels 666a and 666b may be fed from same channel.

It is noted that according to some embodiments, the endoscope tip may include more than one optical window and illuminators on the side and more than one optical window and illuminators on the front.

Sidewalls 362a and 362b may have a form of an essentially flat surface, which assists in directing the cleaning fluid injected from injector channel 666a and 666b towards side optical assembly 256b and 256c and optical windows 252a, 252b, 262a and/or 262b. Lack of such flat surface may result in dripping of the cleaning fluid along the curved surface of tip section 200 of the endoscope without performing the desired cleaning action.

Figure 2B:
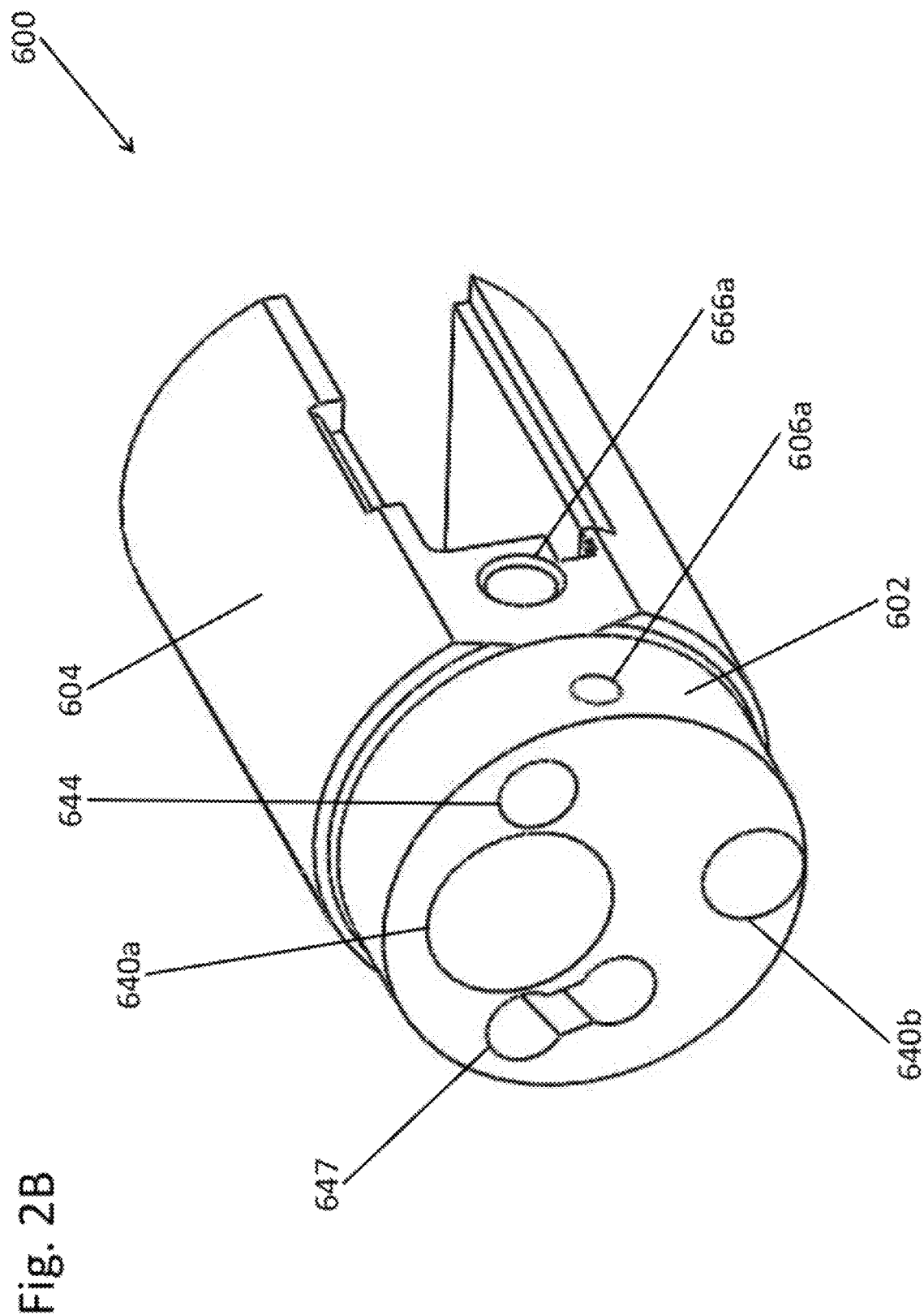
FIG. 2B shows a perspective view of a fluid channeling component of an endoscope assembly according to some embodiments.
Figure 2C:
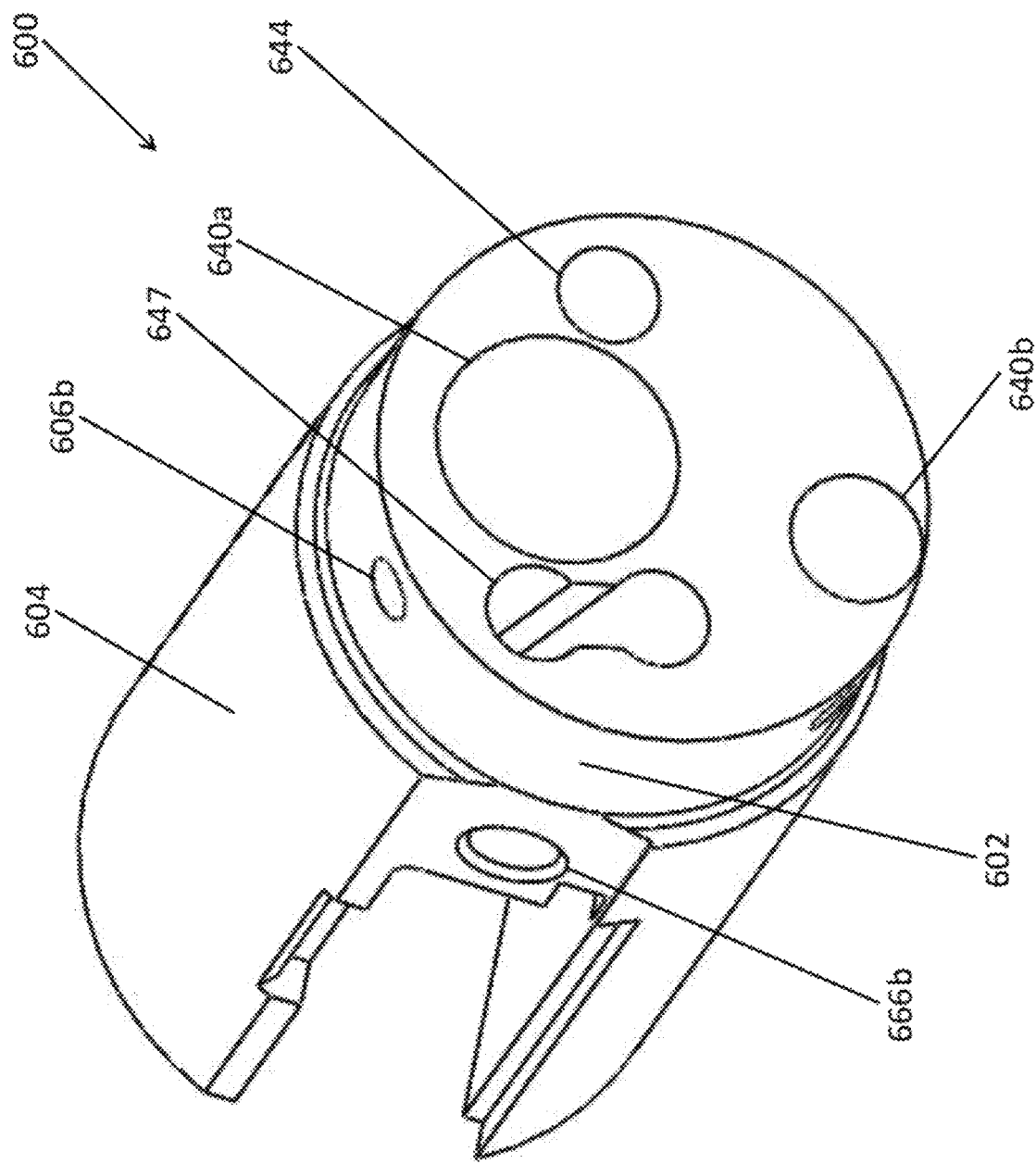
FIG. 2C shows a perspective view of a fluid channeling component of an endoscope assembly according to some embodiments.
Figure 3B:
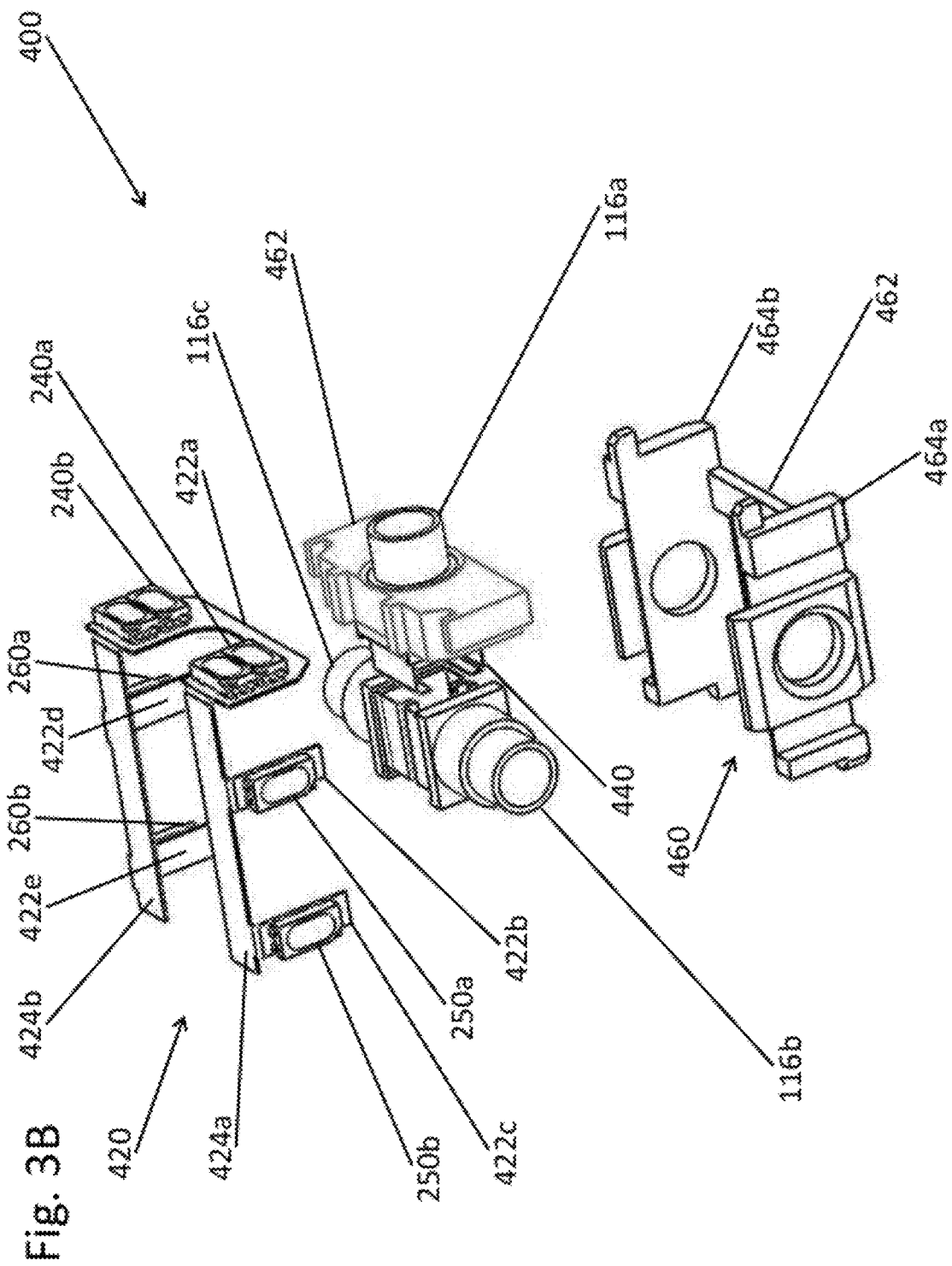
FIG. 3B shows an exploded view of a tip section of a foldable electronic circuit board according to some embodiments.
Figure 3C:
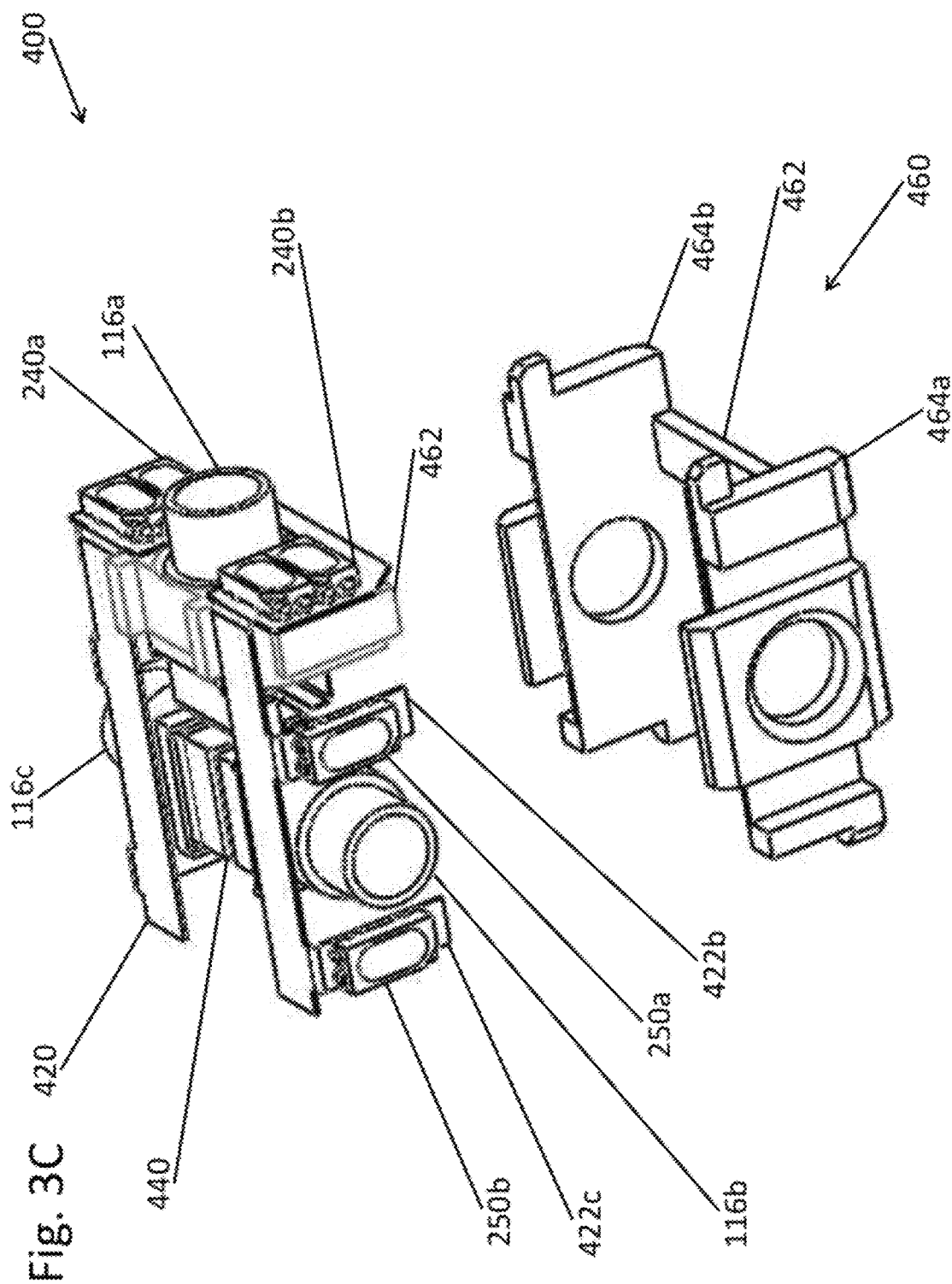
FIG. 3C shows an exploded view of a tip section of a foldable electronic circuit board according to some embodiments.
Figure 3D:
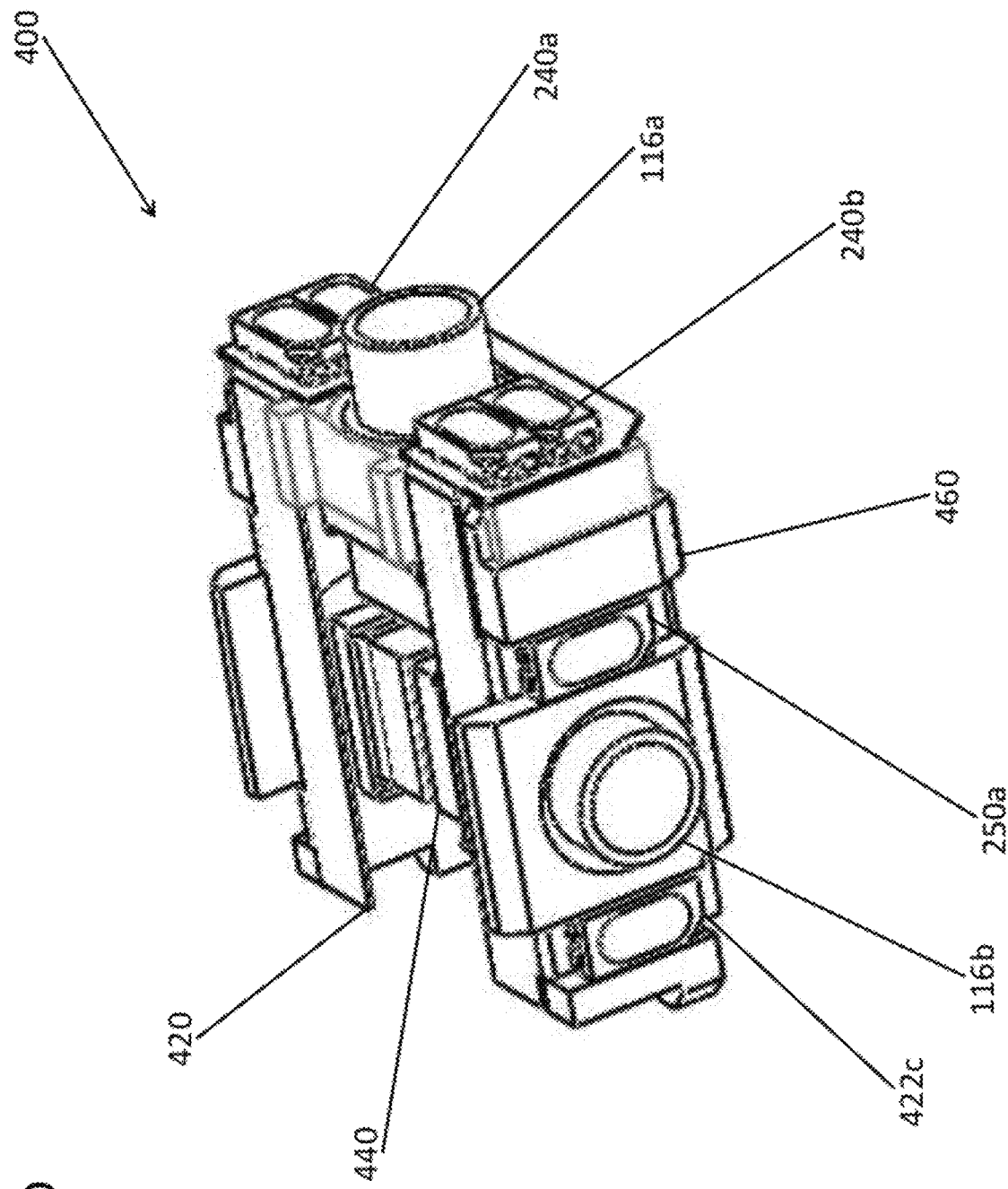
FIG. 3D shows an perspective view of a tip section of a foldable electronic circuit board according to some embodiments.

Reference is now made to FIGS. 2A, 2B and 2C, which show perspective views of a fluid channeling component 600 of an endoscope assembly 100 according to an embodiment.

According to some embodiments, fluid channeling component 600 may be configured as a separate component from foldable electronic circuit board 400 (FIG. 1). This configuration may be adapted to separate the fluid channels and working channels 640a and 640b, which are located in fluid channeling component 600 from the sensitive electronic and optical parts which may be located in the area of foldable electronic circuit board 400 (FIG. 1).

According to some embodiments, fluid channeling component 600 may include a proximal fluid channeling section 602 which may have an essentially cylindrical shape, a primary distal channeling section 604a and a secondary distal channeling section 604b. Primary distal fluid channeling section 604a and secondary distal channeling section 604b may partially continue the cylindrical shape of proximal fluid channeling section 602 and may have a shape of a partial cylinder (optionally elongated partial cylinder). Primary distal fluid channeling section 604a and secondary distal channeling section 604b may form solely two parallel fractions of the cylinder (along the height axis of the cylinder), wherein the third fraction of the cylinder (along the height axis of the cylinder) is missing. Primary distal fluid channeling section 604a and secondary distal channeling section 604b may be integrally formed as a unitary block with proximal fluid channeling section 602. The height of primary distal fluid channeling section 604a and secondary distal channeling section 604b may by higher than that of proximal fluid channeling section 602. In the case of primary distal fluid channeling section 604a and secondary distal channeling section 604b may have the shape of the partial cylinder (for example, partial cylinder having only a fraction of a cylinder shape along one side of the height axis) and provide a space to accommodate foldable electronic circuit board 400 (FIG. 1).

Proximal fluid channeling section 602 may include integrated screw nuts 606a and 606b, which may be configured for securing tip section 200 (FIG. 1) to the endoscope shaft (not shown).

Primary distal fluid channeling section 604a and secondary distal channeling section 604b may include working channels 640a and 640b having a working channel openings 340a, 340b which may be configured for insertion of a medical (such as a surgical) tool, for example, to remove, treat and/or extract a sample of the object of interest found in the colon or its entirety for biopsy.

When endoscope assembly 100 is used within a body cavity such as a colon, the endoscope operator advances the endoscope assembly 100 while viewing images and/or video streams transmitted by front-pointing camera 116a and two side-pointing cameras 116b, 116c. When a polyp or other pathology is discovered on a wall of colon, the endoscope operator may insert one or more medical tools (not shown) through working channel 640a and/or second working channel 640b to remove, treat and/or extract a sample of the polyp or its entirety for biopsy.

Therefore, it may be beneficial if the endoscope tip section includes a second working channel, which enables the endoscope's operator to use an additional medical tool, which may be threaded through the second working channel.

A second working channel, such as second working channel 640b allows the performance of medical procedures (for example more complex procedures) using two medical tools. Second working channel 640b provides the endoscope operator a better access to the object of interest and greater flexibility with operating the medical tools while at the same time viewing the procedure by the front pointing camera 116a (FIG. 1). This substantially increases the performance of the endoscope. Moreover, the two front working channels may be used simultaneously for medical procedures. An example of such procedure may include surgery that requires stitching which can more easily be performed using two tools from two channels.

Advantageously, the configuration of foldable electronic circuit board 400 enables having a slim and compact design improves the performance of the endoscope (particularly, the colonoscope) by allowing the incorporation of additional elements to endoscope tip section 300, for example having an endoscope tip section with additional working channel, which may be used for threading a second medical tool.

Reference is now made to FIGS. 3A, 3B, 3C and 3D, which show exploded views of a foldable electronic circuit board 400 of an endoscope assembly 100 according to an embodiment.

According to some embodiments, foldable electronic circuit board 400 may have several internal parts including a camera circuit board 440, a flexible illumination circuit board 420, a bottom circuit board holder 460 and a front circuit board holder 462.

The internal parts of foldable electronic circuit board 400 may be configured to be assembled, connected or attached together into a condensed structure having a slim and compact design.

Additionally, it should be noted that the internal parts of foldable electronic circuit board 400 may be electrically connected and may be configured to share resources as electrical power and electrical signals.

Camera circuit board 440 may be configured to carry a front-pointing camera 116a and two side-pointing cameras 116b, 116c which may be similar to front-pointing camera 116a and may include a Charge Coupled Device (CCD) or a Complementary Metal Oxide Semiconductor (CMOS) image sensor.

According to some embodiments, side-pointing cameras 116b and 116c may be installed such that their field of views are substantially opposing. However, different configurations and number of side-pointing cameras are possible within the general scope of the current invention.

Flexible illumination circuit board 420, which may be formed as a flexible unitary piece of a PCB layer, may include two main sections 424a and 424b, a front foldable panel 422a and four side foldable panels 422b, 422c, 422d, 422e.

When flexible illumination circuit board 420 is in a folded configuration, front foldable panel 422a and four side foldable panels 422b, 422c, 422d, 422e may be configured to fold downwards forming a right angle with two main sections 424a and 424b.

Front foldable panel 422a, may be configured to carry front illuminators 240a, 240b, which may be associated with front-pointing camera 116a and positioned to essentially illuminate front-pointing camera's 116a fields of view.

When front foldable panel 422a is in a folded configuration, it may form a right angle with main sections 424a and 424b such that it faces forwards, essentially at the same direction of front-pointing camera's 116a and therefore enables front illuminators 240a, 240b, to face the same direction as front-pointing camera 116a and essentially illuminate front-pointing camera's 116a field of view.

Side foldable panels 422b, 422c may be configured to carry side illuminators 250a, 250b respectively, which may be associated with side-pointing camera 116b and positioned to essentially illuminate side-pointing camera's 116b fields of view.

When side foldable panels 422b, 422c are in a folded configuration, side foldable panels 422b, 422c may be configured to form a right angle with main section 424a such that it faces sideways, essentially at the same direction of side-pointing camera 116b and therefore enables side illuminators 250a, 250b, to face the same direction as side-pointing camera 116b and essentially illuminate side-pointing camera's 116b field of view.

Side foldable panels 422d, 422e may be configured to carry side illuminators 260a, 260b respectively, which may be associated with side-pointing camera 116c and positioned to essentially illuminate side-pointing camera's 116c fields of view.

When side foldable panels 422d, 422e are in a folded configuration, side foldable panels 422d, 422e may be configured to form a right angle with main section 424b such that it faces sideways, essentially at the same direction of side-pointing camera 116c and therefore enables side illuminators 260a, 260b, to face the same direction as side-pointing camera 116c and essentially illuminate side-pointing camera's 116c field of view.

Front illuminators 240a, 240b and side illuminators 250a, 250b, 260a and 260b may optionally be discrete illuminators and may include a light-emitting diode (LED), which may be a white light LED, an infrared light LED, a near infrared light LED, an ultraviolet light LED or any other LED.

The term "discrete", concerning discrete illuminator, may refer to an illumination source, which generates light internally—in contrast to a non-discrete illuminator, which may be, for example, a fiber optic merely transmitting light generated remotely.

Bottom circuit board holder 460 may be configured to hold and support flexible illumination circuit board 420 in its desired folded configuration and secure camera circuit board 440 including side pointing cameras 116b and 116c and their corresponding illuminators in place.

Bottom circuit board holder 460 may include a bottom portion 462 and two side portions 464a and 464b formed as a unitary piece of rigid material, such as brass, stainless steel, aluminum or any other material.

Each of side portions 464a and 464b may be perpendicularly connected to bottom portion 462 at each opposite side and may have an aperture configured to fit side pointing cameras 116b and 116c.

Front circuit board holder 462 may be configured work in conjunction with bottom circuit board holder 460 and hold and support flexible illumination circuit board 420 in its desired folded configuration and secure camera circuit board 440 including front pointing camera 116a and its corresponding illuminator in place.

Bottom circuit board holder 460 may be formed as a unitary piece of rigid material, such as brass, stainless steel, aluminum or any other material.

The use of metal for the construction of bottom circuit board holder 460 and front circuit board holder 462 may improve electric conductivity and allow efficient heat dissipation. According to some embodiments, bottom circuit board holder 460 and front circuit board holder 462 may be used as a heat sink for some or all of the electronic components located within foldable electronic circuit board 400, particularly illuminators (such as front illuminators 240a, 240b and side illuminators 250a, 250b, 260a and 260b) and reduce overall temperature of the endoscope tip section 200 (FIG. 1). This may solve or at least mitigate a major problem of raised temperatures of endoscope tip and/or any of its components, particularly when using LED illuminators.

Figure 4B:
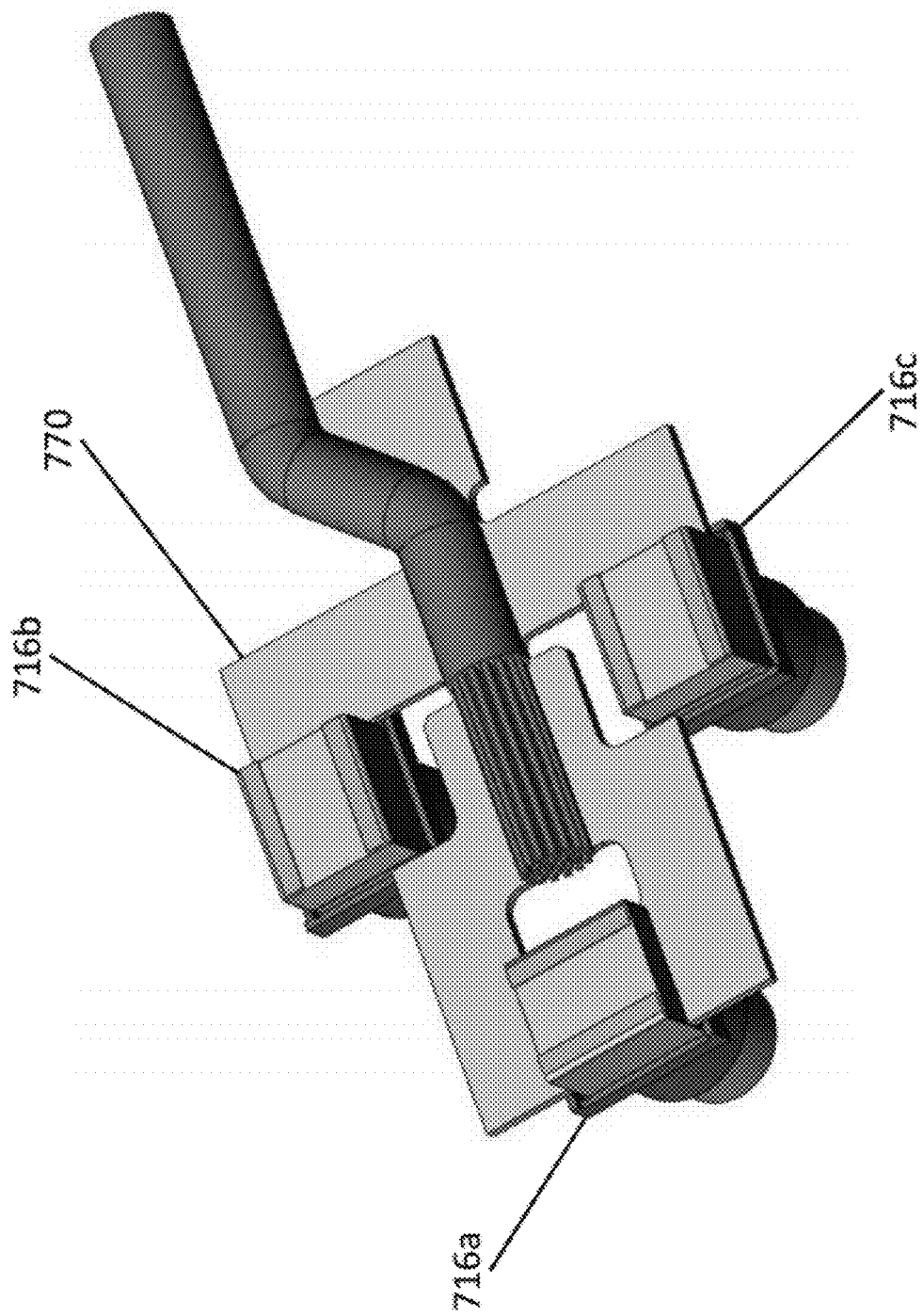
FIG. 4B shows a perspective view of a camera circuit board according to some embodiments.
Figure 4C:
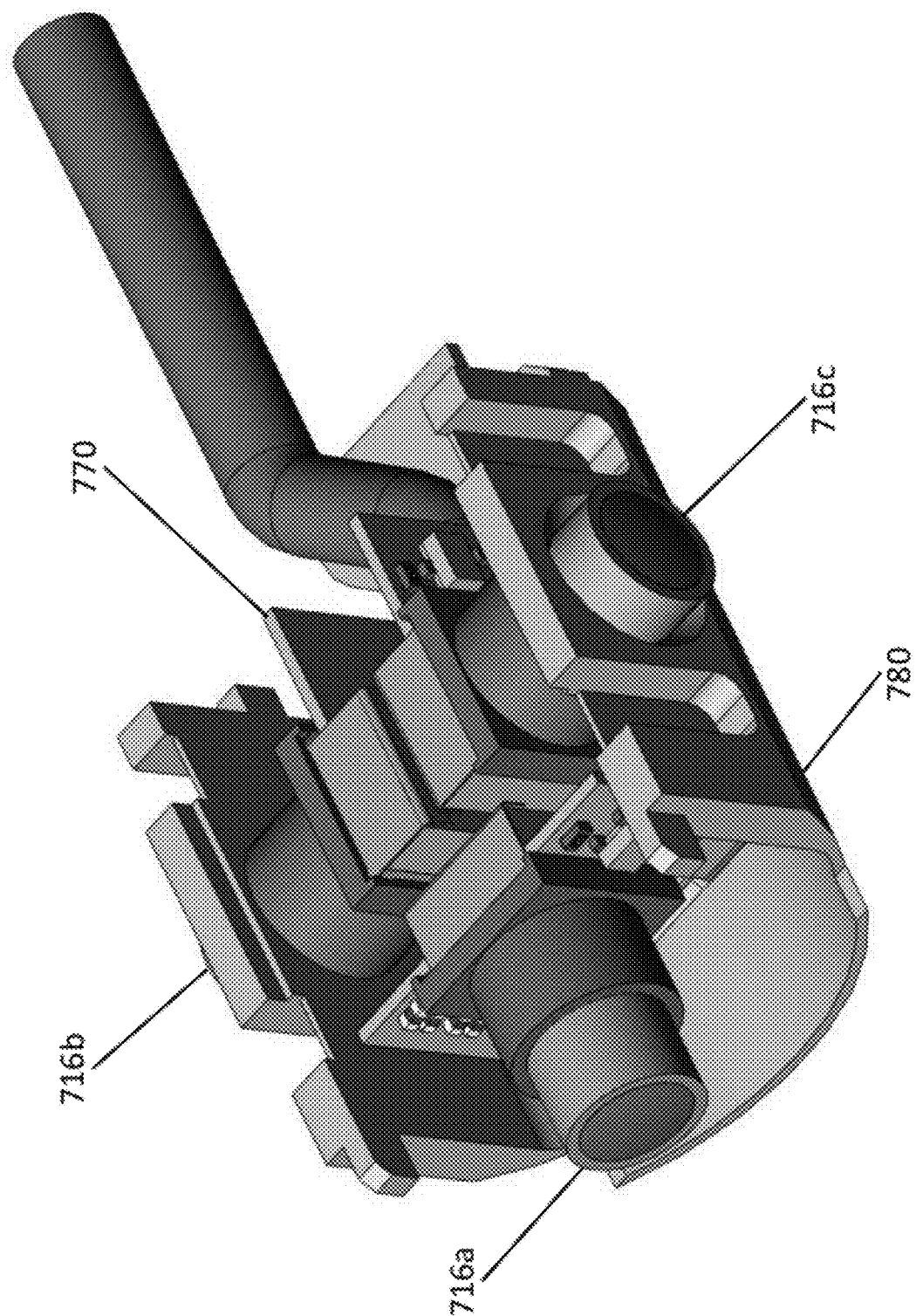
FIG. 4C shows a perspective view of a camera circuit board according to some embodiments.

Reference is now made to FIGS. 4A, 4B and 4C, which show a perspective view of a camera circuit board 770 of an endoscope assembly 800 according to an embodiment.

According to some embodiments, foldable electronic circuit board 700 may have several internal parts including: a camera circuit board 770, a flexible illumination circuit board 720 and a circuit board holder 780.

The internal parts of foldable electronic circuit board 700 may be configured to be assembled, connected or attached together into a condensed structure having a slim and compact design.

Camera circuit board 770 which may be similar to camera circuit board 440 (FIG. 3), may be configured to carry a front-pointing camera 716a and two side-pointing cameras 716b, 716c which may be similar to front-pointing camera 116a (FIG. 1) and may include a Charge Coupled Device (CCD) or a Complementary Metal Oxide Semiconductor (CMOS) image sensor.

According to some embodiments, side-pointing cameras 716b and 716c may be installed such that their field of views are substantially opposing. However, different configurations and number of side-pointing cameras are possible within the general scope of the current invention.

A circuit board holder 780, which is further discussed below, may be configured to hold and support camera circuit board 770.

Figure 5:
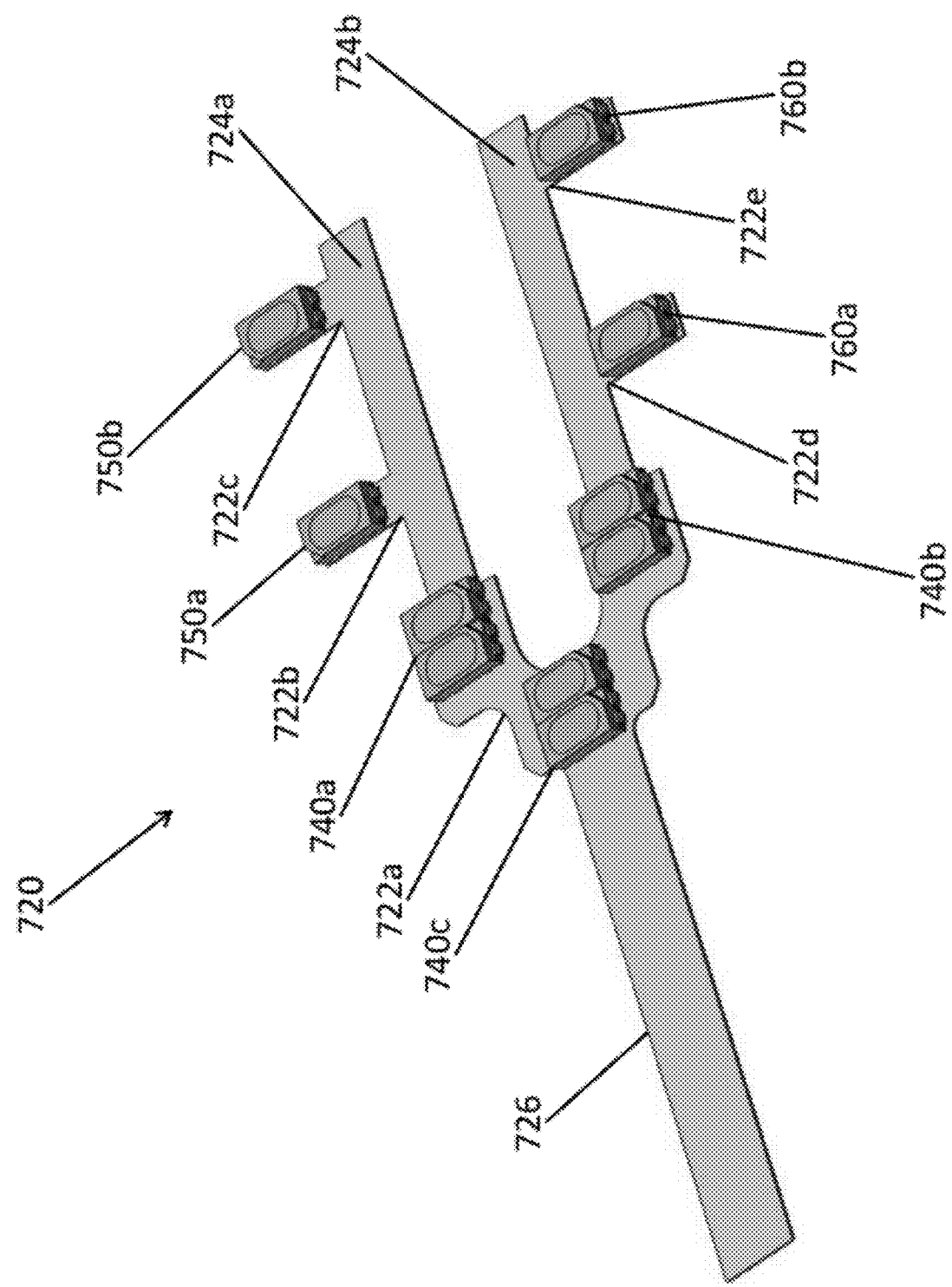
FIG. 5 shows a perspective view of a flexible illumination circuit board according to some embodiments.

Reference is now made to FIG. 5, which shows a perspective view of a flexible illumination circuit board 720 of an endoscope assembly 800 according to an embodiment.

Flexible illumination circuit board 720, which may be formed as a folded unitary piece of a PCB layer, may include illumination circuit board connector 726, two main sections 724a and 724b, a front foldable panel 722a and four side foldable panels 722b, 722c, 722d, 722e.

It is noted that number of front and side foldable panels and associated number of front and side illuminators may vary.

When flexible illumination circuit board 720 is in a folded configuration, front foldable panel 722a and four side foldable panels 722b, 722c, 722d, 722e may be configured to fold downwards forming a right angle with two main sections 724a and 724b.

Front foldable panel 722a, may be configured to carry front illuminators 740a, 740b and 740c, which may be associated with front-pointing camera 716a (FIG. 4) and positioned to essentially illuminate front-pointing camera's 716a (FIG. 4) fields of view.

When front foldable panel 722a is in a folded configuration, it may form a right angle with main sections 724a and 724b such that it faces forwards, essentially at the same direction of front-pointing camera's 716a (FIG. 4) and therefore enables front illuminators 740a, 740b and 740c, to face the same direction as front-pointing camera 716a (FIG. 4) and essentially illuminate front-pointing camera's 716a (FIG. 4) field of view.

Side foldable panels 722b, 722c may be configured to carry side illuminators 750a, 750b respectively, which may be associated with side-pointing camera 716b (FIG. 4) and positioned to essentially illuminate side-pointing camera's 716b (FIG. 4) fields of view.

When side foldable panels 722b, 722c are in a folded configuration, side foldable panels 722b, 722c may be configured to form a right angle with main section 724a such that it faces sideways, essentially at the same direction of side-pointing camera 716b (FIG. 4) and therefore enables side illuminators 750a, 750b, to face the same direction as side-pointing camera 716b (FIG. 4) and essentially illuminate side-pointing camera's 716b (FIG. 4) field of view.

Side foldable panels 722d, 722e may be configured to carry side illuminators 760a, 760b respectively, which may be associated with side-pointing camera 716c (FIG. 4) and positioned to essentially illuminate side-pointing camera's 716c (FIG. 4) fields of view.

When side foldable panels 722d, 722e are in a folded configuration, side foldable panels 722d, 722e may be configured to form a right angle with main section 724b such that it faces sideways, essentially at the same direction of side-pointing camera 716c (FIG. 4) and therefore enables side illuminators 760a, 760b, to face the same direction as side-pointing camera 716c (FIG. 4) and essentially illuminate side-pointing camera's 716c (FIG. 4) field of view.

Front illuminators 740a, 740b and side illuminators 750a, 750b, 760a and 760b may optionally be discrete illuminators and may include a light-emitting diode (LED), which may be a white light LED, an infrared light LED, a near infrared light LED, an ultraviolet light LED or any other LED.

Figure 6B:
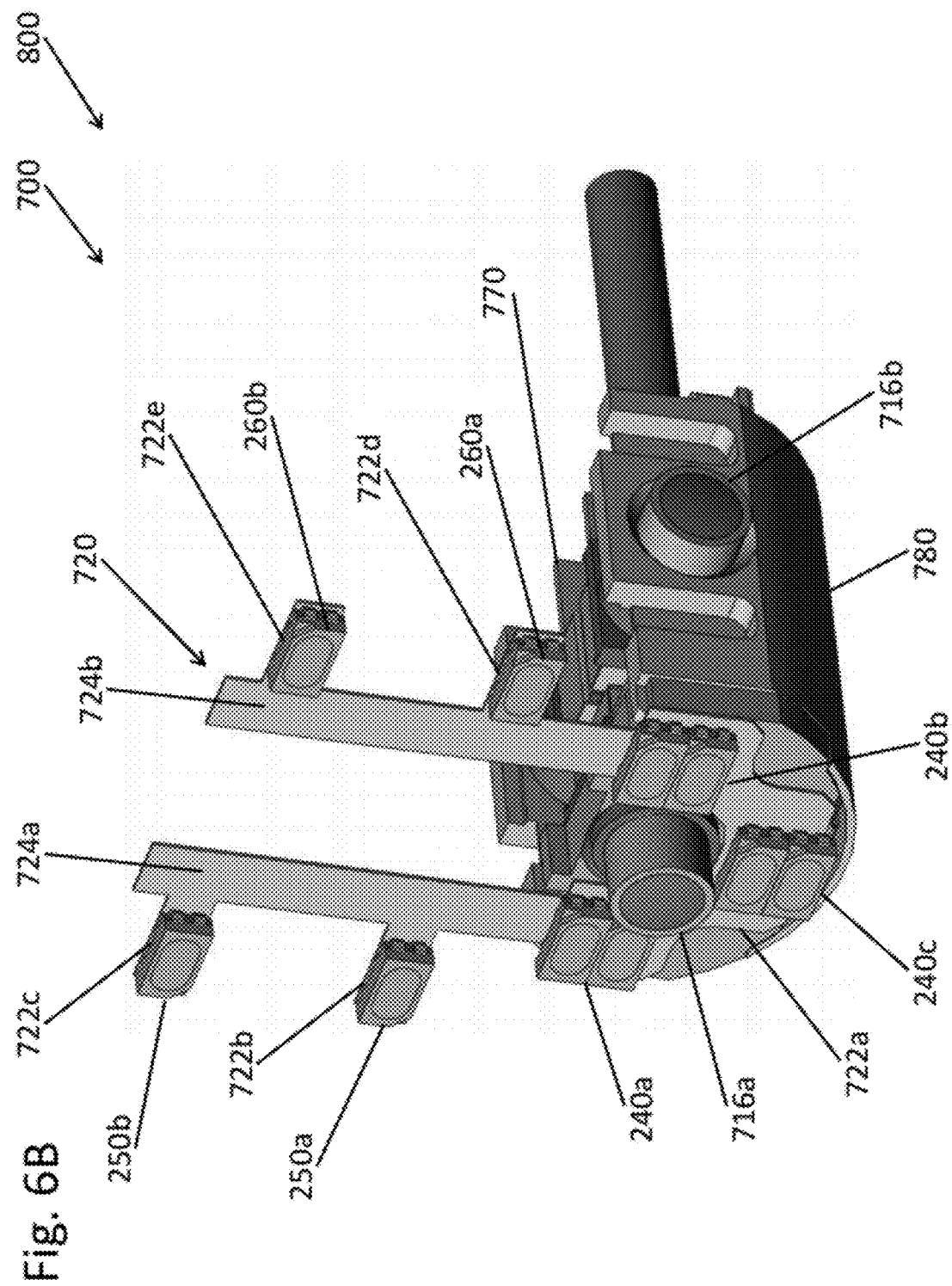
FIG. 6B shows a perspective view of a foldable electronic circuit board according to some embodiments.
Figure 6C:
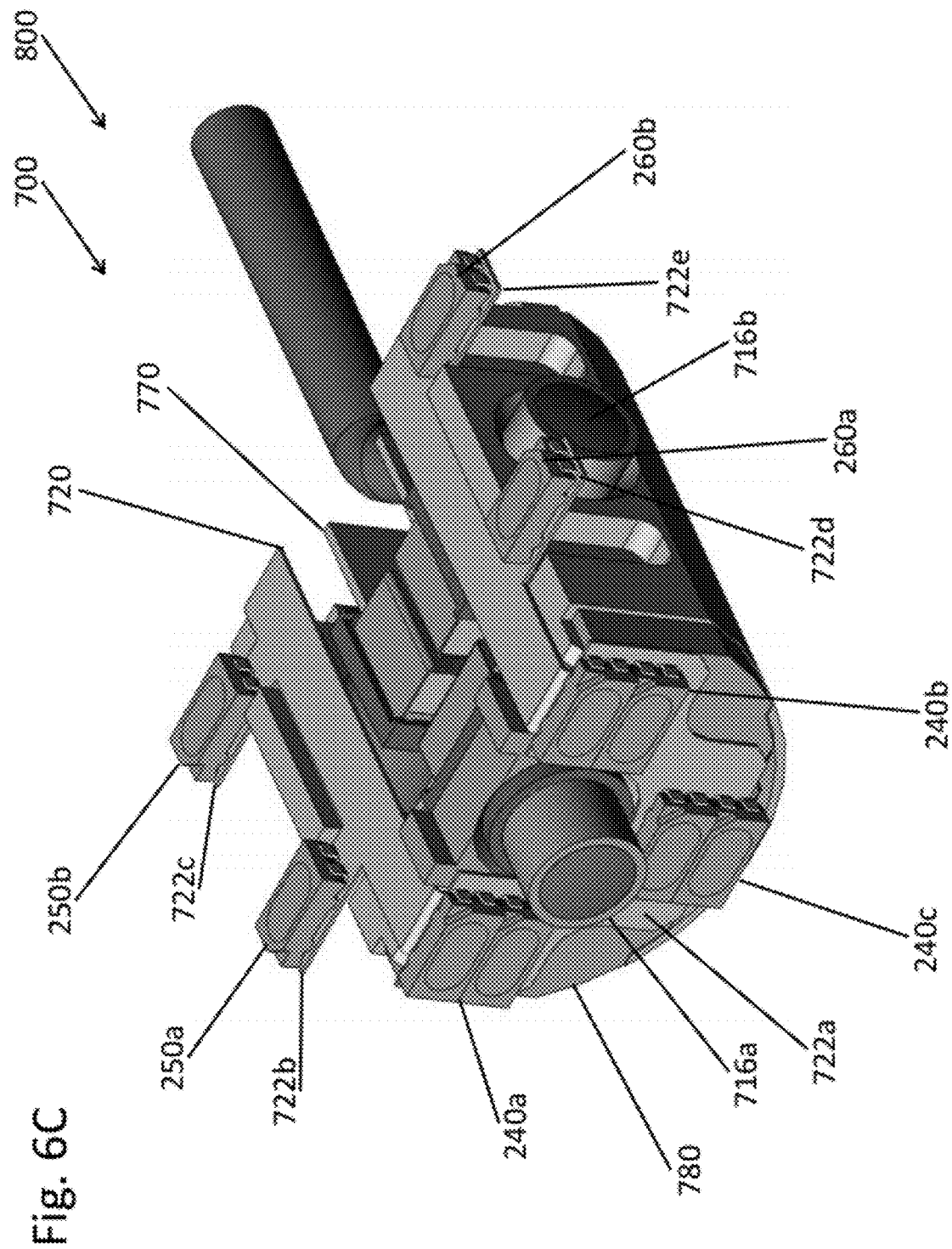
FIG. 6C shows a perspective view of a foldable electronic circuit board according to some embodiments.
Figure 6D:
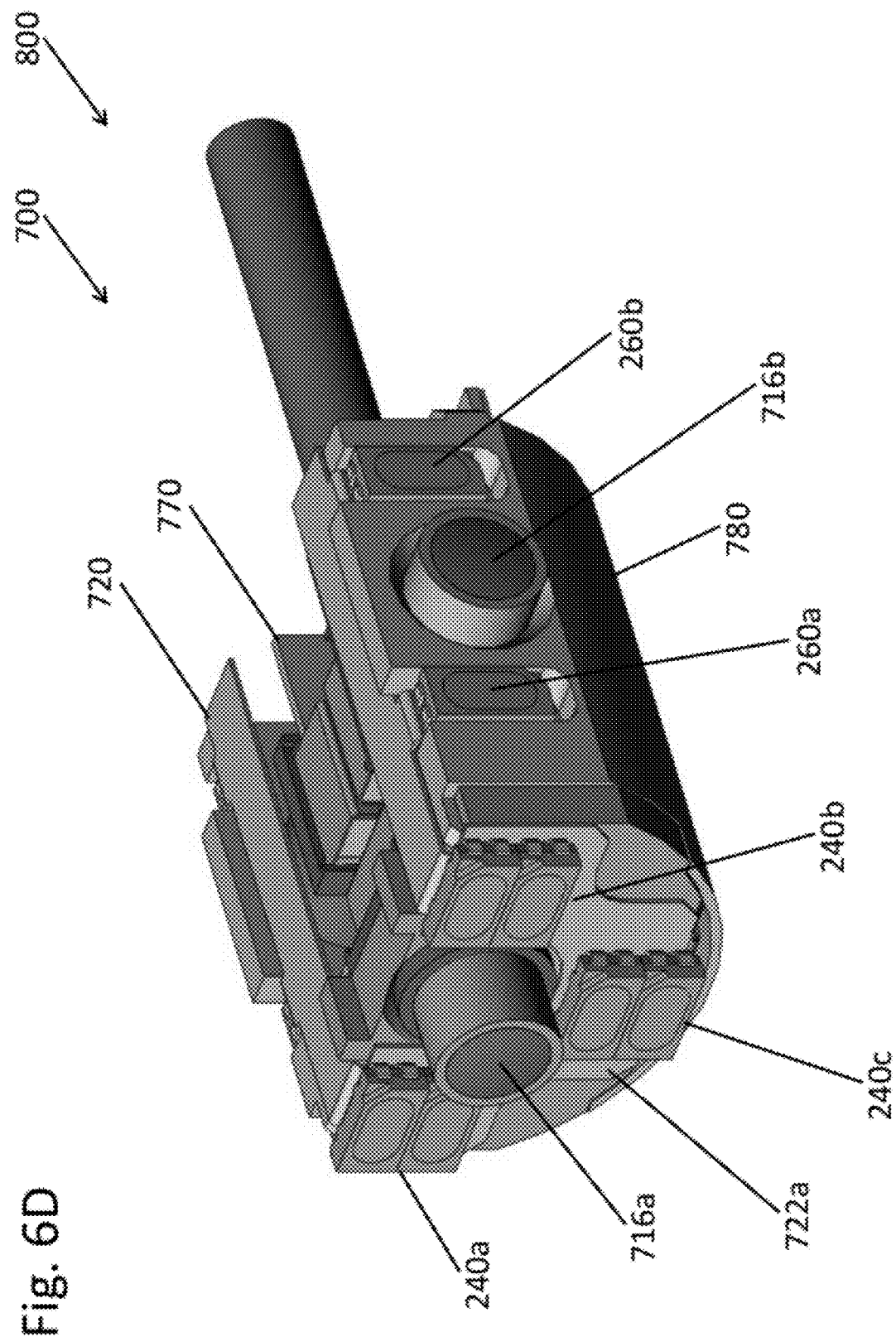
FIG. 6D shows a perspective view of a foldable electronic circuit board according to some embodiments.

Illumination circuit board connector 726 may be configured to connect flexible illumination circuit board 720 to a circuit board holder 780 (FIG. 6).

Reference is now made to FIGS. 6A, 6B, 6C and 6D, which show a perspective view of a foldable electronic circuit board 700 of an endoscope assembly 800 according to an embodiment.

Circuit board holder 780 may be configured to hold and support flexible illumination circuit board 720 in its desired folded configuration and secure camera circuit board 770 including side pointing cameras 716b and 716c and their corresponding illuminators in place.

Circuit board holder 780 may be formed as a unitary piece of rigid material, such as brass, stainless steel, aluminum or any other material.

The use of metal for the construction of circuit board holder 780 may improve electric conductivity and allow efficient heat dissipation. According to some embodiments, circuit board holder 780 may be used as a heat sink for some or all of the electronic components located within foldable electronic circuit board 700, particularly illuminators (such as front illuminators 740a, 740b and side illuminators 750a, 750b, 760a and 760b) and reduce overall temperature of the endoscope tip section. This may solve or at least mitigate a major problem of raised temperatures of endoscope tip and/or any of its components, particularly when using LED illuminators.

Figure 7:
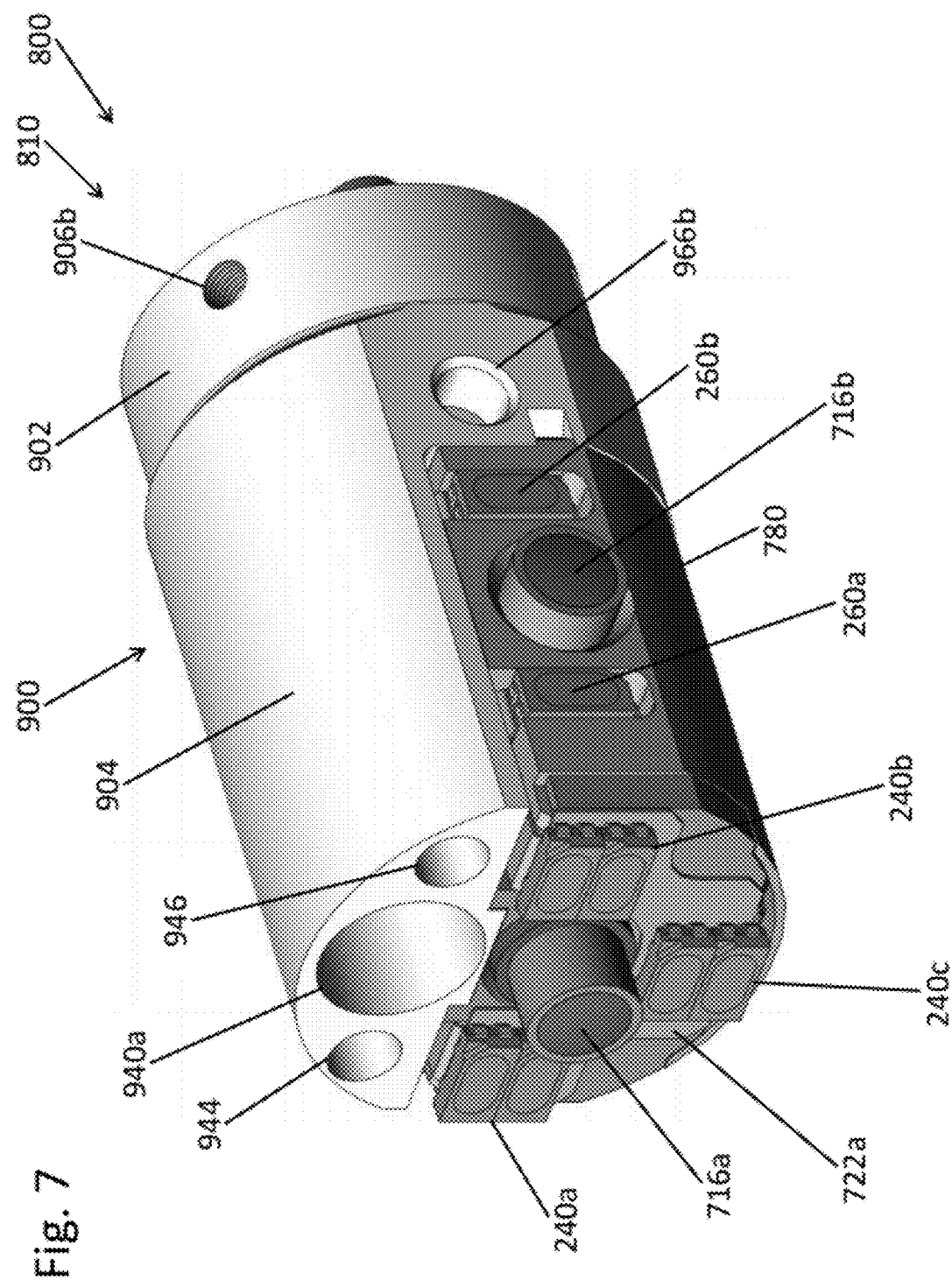
FIG. 7 shows a perspective view of an endoscope tip section according to some embodiments.

Reference is now made to FIG. 7, which shows a perspective view of a tip section 810 of an endoscope assembly 800 according to an embodiment.

According to some embodiments, fluid channeling component 900 may be configured as a separate component from foldable electronic circuit board 700 (FIG. 6). This configuration may be adapted to separate the fluid channels and working channels 940a, which is located in fluid channeling component 900 from the sensitive electronic and optical parts which may be located in the area of foldable electronic circuit board 700 (FIG. 1).

According to some embodiments, fluid channeling component 900 may include a proximal fluid channeling section 902, which may have an essentially cylindrical shape, a primary distal channeling section 904. Primary distal fluid channeling section 904 may partially continue the cylindrical shape of proximal fluid channeling section 902 and may have a shape of a partial cylinder (optionally elongated partial cylinder). Primary distal fluid channeling section 904 may form a fraction of the cylinder (along the height axis of the cylinder), wherein the other fraction of the cylinder (along the height axis of the cylinder) is missing. Primary distal fluid channeling section 904 may be integrally formed as a unitary block with proximal fluid channeling section 902. The height of primary distal fluid channeling section 904 may by higher than that of proximal fluid channeling section 902. In the case of primary distal fluid channeling section 904 may have the shape of the partial cylinder (for example, partial cylinder having only a fraction of a cylinder shape along one side of the height axis) and provide a space to accommodate foldable electronic circuit board 700 (FIG. 6).

Proximal fluid channeling section 902 may include integrated screw nuts 906b, which may be configured for securing tip section 810 to the endoscope shaft (not shown).

Primary distal fluid channeling section 904 may include working channels 940a which may be configured for insertion of a medical (such as a surgical) tool, for example, to remove, treat and/or extract a sample of the object of interest found in the colon or its entirety for biopsy.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

In the description and claims of the application, each of the words "comprise" "include" and "have", and forms thereof, are not necessarily limited to members in a list with which the words may be associated.

What is claimed is:

1. An electronic assembly for a tip section of a multi-camera endoscope, the assembly comprising:
   a front-pointing camera facing a first direction;
   a first side-pointing camera facing a second direction;
   a second side-pointing camera facing a third direction, wherein the second direction is opposite the third direction and wherein the second and third directions are substantially perpendicular to the first direction;
   a camera circuit board configured to communicate with the front-pointing camera, first side-pointing camera, and second side-pointing camera; and
   a flexible illuminator circuit board comprising
      a first section comprising a first plurality of flexible panels;
      a second section comprising a second plurality of flexible panels;
      a third section that is attached to the first and second sections, wherein, in a first configuration, the first section, second section and third section define a first plane;
      a first illuminator mounted on the third section;
      a second illuminator mounted on one of said first plurality of flexible panels;
      a third illuminator mounted on one of said second plurality of flexible panels wherein, upon said flexible illuminator circuit board being folded into a second, operative configuration, the first illuminator is positioned adjacent to the front-pointing camera and defines a second plane orthogonal to the first plane, the second illuminator is positioned adjacent to the first side-pointing camera and defines a third plane orthogonal to the first plane, and the third illuminator is positioned adjacent to the second side-pointing camera and defines a fourth plane orthogonal to the first plane, and wherein said second, third and fourth planes are different.

2. The electronic assembly according to claim 1, further comprising one or more circuit board holders configured to support said flexible illuminator circuit board, said camera circuit board or both.

3. The electronic assembly according to claim 2, wherein said circuit board holder comprises at least one niche configured to accommodate at least one of said illuminators or at least one of said cameras.

4. The electronic assembly according to claim 1, wherein said camera circuit board is a foldable camera circuit board.

5. The electronic assembly according to claim 1, wherein said camera circuit board is configured to carry the front-pointing camera and the two side-pointing cameras.

6. A tip section for a multi-camera endoscope, the tip section comprising the electronic assembly of claim 1 and a fluid channeling component.

7. The tip section according to claim 6, wherein said fluid channeling component comprises:
   at least one front fluid injector configured for cleaning said at least one front-pointing camera or said at least one of front illuminator;
   at least one side fluid injector configured for cleaning said at least one side-pointing camera or said at least one of side illuminator; and
   a front working channel configured for insertion of a medical tool.

8. The tip section according to claim 7, wherein said front and side fluid injectors are connected to a same fluid supply channel.

9. The tip section according to claim 6, wherein said at least one said first illuminator, said second illuminator, and said third illuminator comprises a discrete illuminator.

10. The tip section according to claim 9, wherein said discrete illuminator comprises a light-emitting diode (LED).

11. The tip section according to claim 6, wherein at least one of said first illuminator, said second illuminator, and said third illuminator is configured to emit white light.

12. The tip section according to claim 6, wherein at least one of said first illuminator, said second illuminator, and said third illuminator is configured to emit ultraviolet light.

13. The tip section according to claim 6, wherein at least one of said first illuminator, said second illuminator, and said third illuminator is configured to emit infrared light.

14. The tip section according to claim 6, wherein at least one of said first illuminator, said second illuminator, and said third illuminator is configured to emit near-infrared light.

15. The tip section according to claim 6, wherein said first illuminator, said second illuminator, and said third illuminator are configured to emit light in different wavelengths.

16. The tip section according to claim 6, wherein said front-pointing camera and said side-pointing camera independently comprise a Charge Coupled Device (CCD) or a Complementary Metal Oxide Semiconductor (CMOS) image sensor.

17. The tip section according to claim 6, wherein said endoscope is a colonoscope.

18. The tip section according to claim 6, wherein fields of view of said front-pointing camera and side-pointing camera are at least partially overlapping.

19. The tip section according to claim 6, wherein said at least one of said front and side pointing cameras comprises a lens assembly providing a field of view of at least 90 degrees.

20. The tip section according to claim 6, wherein said at least one of said front and side pointing cameras comprises a lens assembly providing a field of view of at least 120 degrees.

21. The tip section according to claim 6, wherein said at least one of said front and side pointing cameras comprises a lens assembly providing a focal length of approximately 3-100 millimeters.

* * * * *